US008906608B2

(12) United States Patent
Boschetti et al.

(10) Patent No.: US 8,906,608 B2
(45) Date of Patent: Dec. 9, 2014

(54) METHODS FOR REDUCING THE RANGE IN CONCENTRATIONS OF ANALYTE SPECIES IN A SAMPLE

(75) Inventors: Egisto Boschetti, Crossy sur Seine (FR); David Hammond, Laytonsville, MD (US)

(73) Assignees: Bio-Rad Laboratories, Inc., Hercules, CA (US); American National Red Cross, Rockville, MD (US)

( * ) Notice: Subject to any disclaimer, the term of this patent is extended or adjusted under 35 U.S.C. 154(b) by 1418 days.

(21) Appl. No.: 11/495,842

(22) Filed: Jul. 28, 2006

(65) Prior Publication Data
US 2007/0065953 A1 Mar. 22, 2007

Related U.S. Application Data

(63) Continuation of application No. 11/089,128, filed on Mar. 23, 2005, now abandoned.

(60) Provisional application No. 60/643,483, filed on Jan. 12, 2005, provisional application No. 60/587,585, filed on Jul. 12, 2004, provisional application No. 60/582,650, filed on Jun. 23, 2004, provisional application No. 60/559,108, filed on Apr. 2, 2004.

(30) Foreign Application Priority Data

Mar. 23, 2004 (EP) ..................................... 04290775

(51) Int. Cl.
*C12Q 1/68* (2006.01)
*G01N 33/53* (2006.01)

(52) U.S. Cl.
USPC ............................. 435/6.1; 435/7.1; 435/7.2

(58) Field of Classification Search
USPC ............................................. 435/6.1, 7.1, 7.2
See application file for complete search history.

(56) References Cited

U.S. PATENT DOCUMENTS

| 5,010,175 A | 4/1991 | Rutter et al. | |
|---|---|---|---|
| 5,013,669 A | 5/1991 | Peters, Jr. et al. | |
| 5,578,444 A * | 11/1996 | Edwards et al. | 435/6.11 |
| 5,719,060 A | 2/1998 | Hutchens et al. | |
| 5,840,485 A * | 11/1998 | Lebl et al. | 506/3 |
| 6,057,098 A | 5/2000 | Buechler et al. | |
| 6,093,804 A * | 7/2000 | Ralston et al. | 530/416 |
| 6,139,746 A | 10/2000 | Kopf | |
| 6,225,047 B1 | 5/2001 | Hutchens et al. | |
| 6,268,222 B1 * | 7/2001 | Chandler et al. | 436/523 |
| 6,348,318 B1 | 2/2002 | Valkirs | |
| 2002/0077306 A1 * | 6/2002 | Dinkelborg et al. | 514/44 |
| 2002/0127739 A1 | 9/2002 | Pieper | |
| 2003/0003602 A1 | 1/2003 | Vogt et al. | |
| 2003/0036095 A1 | 2/2003 | Tchaga | |
| 2003/0211471 A1 | 11/2003 | Hammond et al. | |
| 2003/0212253 A1 | 11/2003 | Hammond et al. | |
| 2004/0101830 A1 | 5/2004 | Hammond et al. | |
| 2007/0065953 A1 * | 3/2007 | Boschetti et al. | 436/518 |
| 2007/0275753 A1 * | 11/2007 | Griffin et al. | 455/550.1 |
| 2008/0039339 A1 * | 2/2008 | Hassibi et al. | 506/9 |

FOREIGN PATENT DOCUMENTS

| EP | 1006362 A1 | 7/2000 |
|---|---|---|
| JP | 2002-296281 A | 10/2002 |
| WO | WO 99/06833 A1 | 2/1999 |
| WO | 02/48716 A2 | 6/2002 |
| WO | 03/058199 A2 | 7/2003 |
| WO | WO 2004/031730 A2 | 4/2004 |

OTHER PUBLICATIONS

Chalkley et al. Methods in Enzymology. vol. 377: 421-442; 2003.*
Freije Jr., et al., "Activity-based enrichment of matrix metalloproteinases using reversible inhibitors as affinity ligands"; Journal of Chromatography A, Elsevier Science, NL; vol. 1009, No. 1-2; pp. 155-169; XP004447858; ISSN: 0021-9673 (Aug. 2003).
Ferrer I., et al.; "Validation of new solid-phase extraction materials for the selective enrichment of organic contaminants from environmental samples"; TRAC, Trends in Analytical Chemistry, Analytical Chemistry; Cambridge, GB; vol. 18, No. 3, pp. 180-192; XP004161232; ISSN: 0165-9936 (Mar. 1999).
Supplementary European Search Report from EP 05729099.1, dated Oct. 27, 2011.
Notice of Reasons for Rejection from JP 2007-505108, dated Jun. 21, 2010.

* cited by examiner

*Primary Examiner* — Ardin Marschel
(74) *Attorney, Agent, or Firm* — Kilpatrick Townsend & Stockton LLP

(57) ABSTRACT

The present invention relates to the fields of molecular biology, combinatorial chemistry and biochemistry. Particularly, the present invention describes methods and kits for dynamically reducing the variance between analyte taken from complex mixtures.

40 Claims, 9 Drawing Sheets

METHODS FOR REDUCING THE RANGE IN CONCENTRATIONS OF ANALYTE SPECIES IN A SAMPLE

CROSS-REFERENCES TO RELATED APPLICATIONS

This application is a continuation of application Ser. No. 11/089,128, filed Mar. 23, 2005, now abandoned, which claims the benefit of provisional application Ser. No. 60/559,108, filed Apr. 2, 2004, provisional application Ser. No. 60/582,650, filed Jun. 23, 2004, provisional application Ser. No. 60/587,585, filed Jul. 12, 2004, provisional application Ser. No. 60/643,483, filed Jan. 12, 2005, and European patent application Ser. No. 04290775.8, filed Mar. 23, 2004, the disclosures of which are incorporated in their entireties herein by reference.

FIELD OF THE INVENTION

The present invention relates to the fields of combinatorial chemistry, protein chemistry and biochemistry.

BACKGROUND OF THE INVENTION

Proteomics seeks to generate an identity profile of the entire proteome of an organism and, through analysis of this information, to identify potential diagnostic and therapeutic entities. Current technologies for resolving protein mixtures include two-dimensional gel electrophoresis and multi-dimensional liquid chromatography. Both of these techniques may be coupled to mass spectrometry. An example of this approach is the resolution and identification of 1,484 proteins in yeast (Washburn et al., *Nat. Biotechnol.* 19(3): 242-2471 (2001)). Another example of methodology that separates and identifies proteins is a modified version of the yeast two-hybrid screening assay developed by Uetz et al. (Uetz et al., *Nature* 403(6770): 623-627 (2000)) and Ito et al. (Ito et al., *Proc. Natl. Acad. Sci. USA* 98(8): 4569-4574 (2001)), which identified over 4,000 protein-protein interactions in *Saccharomyces cerevisiae*. A quantitative methodology for protein separation and identification is isotope coded affinity tag (ICAT), developed by Aebersold and colleagues (Smolka et al., *Anal. Biochem.* 297(1): 25-312 (2001)). ICAT involves site-specific, covalent labeling of proteins with isotopically normal or heavy reagents to quantitate levels of protein expression.

Complex protein mixtures may also be separated on libraries of combinatorially-generated ligands. Following exposure of an entity molecule to a combinatorial library, the entity may bind to ligands in the library. Detection of the bound entity may be accomplished when a purified, radiolabeled initial entity is used (Mondorf et al., *J. Peptide Research* 52: 526-536 (1998)). Other methods include detection by an antibody against the entity (Buettner et al., *International Journal of Peptide & Protein Research* 47: 70-83 (1996); Furka et al., *International Journal Peptide Protein Research* 37(6): 487-493 (1991); and Lam et al., (1991) supra). Ligands to multiple entities can be detected using beads immobilized on an adhesive in combination with a subtractive screening method. This is referred to as the QuASAR method (International (PCT) Patent Application WO 01/40265) and was used to detect ligands that bound to virus and prion protein.

FIoNA assay technology (Hammond et al International (PCT) Patent Application WO 04/007757) and other combinatorial techniques can identify a ligand:entity interation. The FIoNA assay technology identifies proteins from mixtures based on chemical, physical, biological, and/or biochemical function and not merely on their ability to bind a ligand within the library. Thus, the goal of FIoNA is to identify a ligand-support that binds a desired property, then to decode the ligand on the appropriate bead, and synthesize the bead in appropriate amounts to purify the one, or few proteins with the desired activity using current proteomic methods.

The full analysis of analytes in complex biological extracts is hindered by the large difference in concentration between individual analytes. In most biological mixtures some analytes are present at high concentration and others only present at trace-levels. As a result, the concentration of analytes may not be adapted to the dynamic range of a given analytical method. That is to say, the difference in the signal strengths produced by the most abundant and least abundant analyte species in a sample generally is wider than the ability of the analytical method to detect and accurately measure. For example, highly concentrated proteins may saturate the detection system and very low concentrations may be below the sensitivity of the analytical method, as occurs in human serum where the difference in concentration between the most abundant protein (albumin—tens of mg/ml) and the least abundant (e.g., IL-6—less than 1 pg/ml) may reach factors as high as hundreds of millions.

Two ways are currently followed to deal with this gap: the first is to design more adapted instruments and the second is to alter the sample for analysis.

One method of altering the sample is to deplete the sample of the more abundant species, thereby making the less abundant species more available for detection. This method involves, for example, the use of linker moieties, such as antibodies or specific dyes, that are directed to particular species in the sample. For example, in the case of plasma, the abundant proteins include albumin, immunoglobulins, fibrinogen, and alpha-1 proteinase inhibitor. Immunoaffinity columns are expensive, seldom totally specific for their target and will remove proteins associated with the target proteins. Moreover, once the most abundant proteins are removed, another set becomes the most abundant, which then creates the need to develop additional affinity columns. In addition, biological samples from different tissues within the same species and tissues from different species may have a completely different set of most abundant proteins. This method also suffers from the fact that elimination of some analyte species also eliminates species that interact with them. Thus some species that may be of interest are eliminated. While eliminating proteins of high abundance may help in some instances, this approach does not result in the detection of very low abundance proteins whose concentration is still below the sensitivity of the instrument to detect. Moreover, highly abundant species are represented by several proteins (even several dozen in some situations) and therefore a number of specific methods would have to be designed to address each different abundant species. Therefore, this method does not substantially compress the range of concentrations between the remaining analyte species.

Another method is to fractionate the sample, typically by chromatography. This method results in the compartmentalization of classes of analytes into different fractions based on similar biochemical properties. For example, ion exchange chromatography will compartmentalize proteins into fractions based on charge, while size exclusion chromatography compartmentalizes proteins based on size. Therefore, these methods may reduce the concentration range of the analytes, but at the cost of substantially decreasing the diversity of the population of analyte species within each compartment.

SUMMARY OF THE INVENTION

This invention provides a method to compress the range of concentrations between different analyte species in a complex sample while substantially maintaining the diversity of the population of analyte species in the sample. More specifically, the method decreases the concentration of more abundant species relative to the concentration of less abundant species but does not involve substantially eliminating from the sample analyte species based on physical-chemical characteristics.

As noted, each analytical technology has a dynamic range of detection. When the amount of an analyte in a sample is above the dynamic range, its signal saturates the detection system and the amount cannot be measured accurately. When the amount of an analyte in a sample is below the sensitivity range of the detection system, the analyte also cannot be detected. Furthermore, signals from abundant analytes may interfere with the ability to detect less abundant analytes even if the less abundant analytes are within the dynamic range of detection. The methods of this invention compress the range of concentrations between analyte species in a sample. This allows one to provide an increased number of analyte molecules to the detector system so as to be above the sensitivity threshold of detection, while, as the same time, to decrease the amount of the abundant analtyes submitted for detection so that there is considerably less saturation of the detection system by abundant analytes and, consequently, reduced interference with the ability to detect less abundant species above the sensitivity threshold. The result is an ability to detect more analyte species in a sample. Using this method, one can detect at least 1.5 times as many species from serum by mass spectrometry. Frequently, this number is between two and four times as many detectable species.

The method of this invention contrasts with other methods of manipulating a sample for detection. For example, depletion of selected abundant species does not significantly decrease the range in concentrations of the wide number of species in a sample. Fractionation decreases the range in concentration of analytes, but does so by substantially decreasing the diversity of the species within the population of the compartment.

This invention achieves this result by exposing a complex sample to a selected amount of a library containing many different binding moieties. Both variables—diversity of the library constituents and amount of the library used—can be manipulated to advantage in this invention. By manipulating the diversity of the different binding moieties to which the sample is exposed, it is possible to bind species throughout the range of concentrations, that is, both abundant and rare species. Also, the larger the number of different binding moieties used, the larger the number of species within the sample population it is possible to capture.

The amount of the library also must be selected so that the binding moieties are saturated by at least the more abundant species in the sample. In this way, the relative amounts of abundant and rare species in the sample that are captured will be much closer than their relative concentrations in the original sample. This results in compression of the concentration range, which allows a greater number of signals produced by both abundant and rare species during detection that are within the dynamic range of the selected detection system.

It is an object of this invention to increase significantly the number of species detectable in a sample and, in particular, the discovery of new species within a sample. Certain kinds of libraries of binding moieties are preferred for achieving this end. In particular, one can best achieve this end by using libraries of large numbers of different binding moieties that have not been pre-selected for their ability to bind particular analytes in a sample. Such libraries are referred to herein as "non-selective" libraries. (The fact that binding specificities of some binding moieties in such a library may be apparent after using the library does not render the same library "selective.") Using such libraries increases the likelihood of capturing species throughout the population without discrimination. Thus, for example, a library of antibodies in which each antibody is directed to a known binding partner will select only the species to which each antibody is directed; in contrast a germline antibody library of the same size does not contain antibodies that bind to pre-selected analytes. Such a library is more likely to select species not known to exist in a sample. One can create non-selective libraries by employing combinatorial chemistry or by randomly assembling chemical moieties. Furthermore, by increasing the size of a library, whether selective or non-selective, one can increase the number of different analyte species in a sample captured and detected. Examples of non-selective libraries of binding moieties include germ line antibody libraries, phage display libraries of recombinant binding proteins, dye libraries and non-combinatorial libraries in which the binding specificity of the members is not pre-selected, combinatorial libraries of various sorts and portions thereof.

It should also be noted that the amount of concentration compression depends upon the relative amounts of binding moieties and analytes in the sample. At one extreme, the relative amount of binding moieties to analytes may be so large that the binding moieties are able to capture all of the analytes in the sample. In this case, there is no compression of the analyte concentration range. At the other extreme, the relative amount of binding moieties to the analytes may be so small, that every analyte species saturates the ability of the binding moieties to bind. In this case, theoretically, the amount of each analyte species captured is the same, and the range in analyte concentration is compressed to equality. This extreme is particularly useful when the goal is to detect as many species as possible. Between these two extremes is the situation in which the more abundant species saturate the binding moieties, while the less abundant species do not saturate the binding moieties. In this case, there is little difference between the range in concentration of abundant analytes, while differences in concentration of the less abundant species remain. This result is particularly useful for comparing the relative concentrations of analyte species between two different sample classes. For example, in biomarker discovery, samples taken from organisms having two different phenotypic states (e.g., cancer versus non-cancer) are compared to identify analyte species that are differentially present between the two states. By preserving the concentration differences between rare species, the methods of this invention allow one to find biomarkers among these rare analytes. In one embodiment, the ratio of binding moieties to analyte species in the sample is at most 1:500 and, more preferably, at most 1:50 or at most 1:5.

This invention provides a method to reduce the range of concentrations between different analyte species in a complex sample while substantially maintaining the diversity of the population of analyte species in the sample. In a preferred embodiment of the present invention, a method is provided comprising the steps of (a) providing a first sample comprising a plurality of different analyte species present in the first sample in a first range of concentration; (b) contacting the first sample with an amount of a library comprising at least 100 different binding moieties; (c) capturing amounts of the different analyte species from the first sample with the different binding moieties and removing unbound analyte species; and (d) isolating the captured analyte species from the binding moieties to produce a second sample comprising a plurality of different analyte species present in the second sample in a second range of concentrations. The amount of the library is selected to capture amounts of the different analyte species so that the second range of concentrations is less than the first range of concentrations.

The first sample comprises at least 100, at least 1,000, at least 10,000, at least 100,000, at least 1,000,000 or at least 10,000,000 different analyte species. In some embodiments, the library comprises at least 1,000, at least 10,000, at least 100,000, at least 1,000,000 or at least 10,000,000 different binding moieties.

Preferably, the binding moieties comprise bio-organic polymers. Preferably, the bio-organic polymers are selected from the group consisting of peptides, oligonucleotides and oligosaccharides. In another embodiment of the present invention, the binding moieties are selected from the group consisting of antibodies and aptamers.

In a preferred embodiment of the present invention, the binding moieties are bound to a solid support or supports. Preferably, the solid support or supports is a collection of beads or particles. Each bead or particle can be attached to a substantially different binding moiety. Also, a plurality of different binding moieties can be attached to the same bead or particle. Preferably, the beads or particles have a diameter of less than 1 µm. The beads or particles can be formed milling microparticulate beads using a method selected from the group consisting of crushing, grinding and sonicating. In a preferred embodiment of this method, the particles are coupled to a second solid support to form an array or dipstick. Preferred microparticulate beads are a polymeric matrix formed from a natural or synthetic polymer.

In another preferred embodiment of the present invention, the solid support or supports is selected from the group consisting of fibers, monoliths, membranes and plastic strips.

In a preferred embodiment of the present invention, the library contacting a first sample is a non-selective library. Many non-selective libraries can be used to practice the methods of the present invention. A preferred non-selective library can be selected from the group consisting of a germ line antibody library, a phage display library of recombinant binding proteins, a dye library or a non-combinatorial library in which the binding specificity of the members is not preselected, a combinatorial library and portions thereof.

Preferably, the different binding moieties are comprised in a complete or incomplete combinatorial library. A preferred combinatorial library is a hexapeptide library.

In one embodiment of the present invention, the second sample has a diversity of analyte species that is substantially the same as the first sample.

Many samples can be used to practice the methods of the invention. In a preferred embodiment of the present invention, the sample is selected from the group consisting of amniotic fluid, blood, cerebrospinal fluid, intraarticular fluid, intraocular fluid, lymphatic fluid, milk, perspiration plasma, saliva semen, seminal plasma, serum, sputum, synovial fluid, tears, umbilical cord fluid, urine, biopsy homogenate, cell culture fluid, cell extracts, cell homogenate, conditioned medium, fermentation broth, tissue homogenate and derivatives of these.

In one embodiment, the method of the present invention comprises the step of detecting analyte species in the second sample. Preferably, detecting the analytes is done by using a method selected from the group of colorimetric, spectrophotometric, magnetic resonance, ellipsometric, mass spectroscopic, electrophoretic, chromatographic, enzymatic, and sequence analysis.

Optionally, the method of the present invention further comprise the step of fractionating the analytes in the second sample based on a physical or chemical property or the step of identifying at least one of the isolated analytes. Preferably, fractionating the analytes comprises segregating the analytes using a technique selected from the group consisting of chromatography, electrophoresis, capillary electrophoresis, filtration and precipitation.

In one embodiment of the present invention, the method further comprises the step of contacting a biospecific binding moiety with the second sample and determining whether the biospecific binding moiety has captured an analyte species from the second sample.

Removing unbound analytes may comprise the step of washing the captured analytes with a wash buffer.

The methods of this invention can be practiced using different analytes. In a preferred embodiment of the present invention, the analytes are selected from the group consisting of polypeptides, nucleic acids, complex carbohydrates, complex lipids, synthetic inorganic compounds and synthetic organic compounds.

The present invention also provides a method for identifying a diagnostic biomarker. In a preferred embodiment, the method comprises the steps of (a) providing a first set of biosamples from a first set of organisms having a first phenotype; (b) providing a second set of biosamples from a second set of organisms having a second phenotype; (c) performing the method for reducing the range of concentrations between different analyte species in a sample as described herein (claim 1) on each of the biosamples, thereby creating a third and fourth set of biosamples, respectively; (d) detecting analyte species in each of the third and fourth set of biosamples; and (e) identifying at least one analyte species that is differentially present in the third and fourth set of biosamples, whereby the at least one analyte species is a biomarker for distinguishing the first phenotype from the second phenotype. In a preferred embodiment step (e) of this method comprises identifying a biomarker profile that provides better predictive power than any one of the biomarkers in the profile alone.

The invention further provides a method for reducing the relative amounts of analytes in a sample. In a preferred embodiment of the present invention, the method comprises the steps of (a) providing a first sample comprising a first plurality of different analytes having a first variance in amounts; (b) contacting the first sample with a plurality of different binding moieties, each binding moiety present in a determined amount; (c) capturing a portion of the first different analytes from the first sample with the different binding moieties and removing uncaptured analytes; and (d) isolating the captured analytes from the binding moieties to produce a second sample comprising a second plurality of different analytes having a second variance in amounts. The determined amount of each of the plurality of different binding moieties is selected to capture amounts of the different analytes whereby the second variance in amounts is less than the first variance in amounts.

The present invention also provides kits for detecting a plurality of analytes in a sample. In a preferred embodiment of the present invention, a kit comprises a container comprising a library of at least 100 different binding moieties and instructions for using the library to perform a method of the present invention. Preferably, the binding moieties are coupled to a solid support or supports. The library may also comprise a hexapeptide combinatorial library or a portion thereof, wherein the hexapeptides are attached to particles.

Optionally, the kits of the present invention comprise a binding buffer for capturing analytes with the binding moieties or an elution buffer for eluting captured analytes from the binding moieties. Additional kit embodiments of the present invention include optional functional components that would allow one of ordinary skill in the art to perform any of the method variations described herein.

The present invention also provides for libraries comprising binding moieties. In a preferred embodiment of the present invention, a library comprises at least 100 different binding moieties, wherein a plurality of different binding moieties are attached to the same solid support or supports. Preferably, the binding moieties comprise a combinatorial hexapeptide library or a portion thereof.

DEFINITIONS

Figure 1:
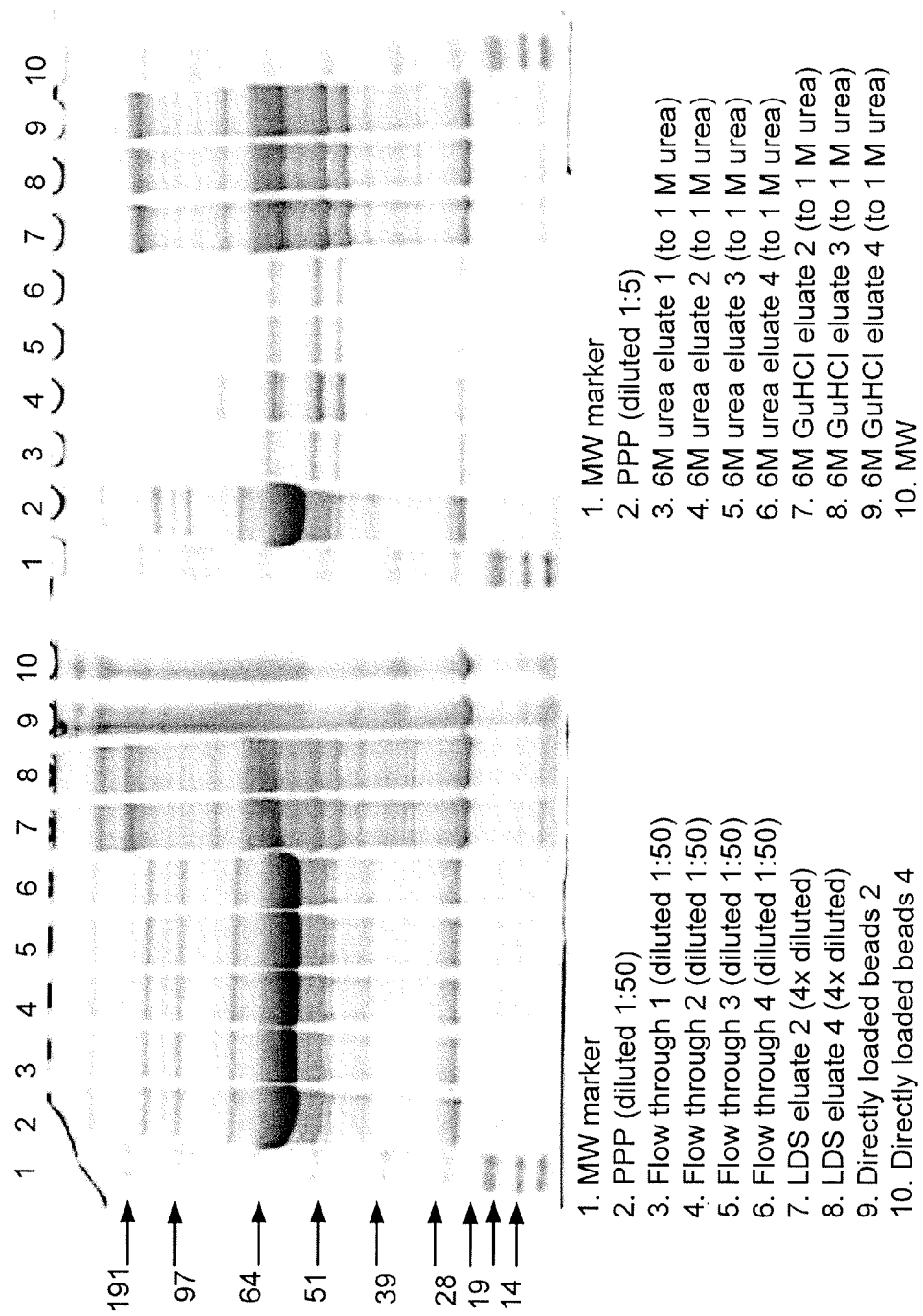
FIG. 1 depicts an analysis showing the result of the incubation of a combinatorial ligand library of the invention with plasma. The library was incubated with plasma according to the methods described in Example 2.

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics*, 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

"Analyte" refers to any molecular moiety capable of binding to a binding moiety of the present invention in a manner that is not completely disrupted by contact with a wash solution as described herein. "Captured analyte" is any analyte bound by a binding moiety of the present invention after contact with a wash solution.

"Adsorbent" refers to any material capable of binding an analyte (e.g., a target polypeptide). "Chromatographic adsorbent" refers to a material typically used in chromatography. Chromatographic adsorbents include for example, ion exchange materials, metal chelators, hydrophobic interaction adsorbents, hydrophilic interaction adsorbents, dyes, and mixed mode adsorbents (e.g., hydrophobic attraction/electrostatic repulsion adsorbents). "Biospecific adsorbent" refers to an adsorbent comprising a biomolecule, e.g., a nucleotide, a nucleic acid molecule, an amino acid, a polypeptide, a simple sugar, a polysaccharide, a fatty acid, a lipid, a steroid or a conjugate of these (e.g., a glycoprotein, a lipoprotein, a glycolipid). In certain instances the biospecific adsorbent can be a macromolecular structure such as a multiprotein complex, a biological membrane or a virus. Examples of biospecific adsorbents are solid supports coupled to antibodies, receptor proteins, lectins and nucleic acids. Biospecific adsorbents typically have higher specificity for a target analyte than a chromatographic adsorbent. Further examples of adsorbents for use in SELDI can be found in U.S. Pat. No. 6,225,047 (Hutchens and Yip, "Use of retentate chromatography to generate difference maps," May 1, 2001).

Binding moieties may exist and interact with analytes detectable using the present invention in any physical state compatible with formation of molecular interactions, including gaseous, aqueous and organic suspensions and emulsions and, most preferably in a liquid state.

"Solid support" refers to any insoluble material including particles (e.g., beads), fibers, monoliths, membranes, filters, plastic strips and the like.

"Protein biochip" refers to a biochip adapted for the capture of polypeptides. Many protein biochips are described in the art. These include, for example, protein biochips produced by Ciphergen Biosystems (Fremont, Calif.), Packard BioScience Company (Meriden Conn.), Zyomyx (Hayward, Calif.) and Phylos (Lexington, Mass.). Examples of such protein biochips are described in the following patents or patent applications: U.S. Pat. No. 6,225,047 (Hutchens and Yip, "Use of retentate chromatography to generate difference maps," May 1, 2001); International publication WO 99/51773 (Kuimelis and Wagner, "Addressable protein arrays," Oct. 14, 1999); International publication WO 00/04389 (Wagner et al., "Arrays of protein-capture agents and methods of use thereof," Jul. 27, 2000) and International publication WO 00/56934 (Englert et al., "Continuous porous matrix arrays," Sep. 28, 2000).

"Surface-Enhanced Neat Desorption" or "SEND" is a version of SELDI that involves the use of probes ("SEND probe") comprising a layer of energy absorbing molecules attached to the probe surface. Attachment can be, for example, by covalent or non-covalent chemical bonds. Unlike traditional MALDI, the analyte in SEND is not required to be trapped within a crystalline matrix of energy absorbing molecules for desorption/ionization. "Energy absorbing molecules" ("EAM") refer to molecules that are capable of absorbing energy from a laser desorption/ionization source and thereafter contributing to desorption and ionization of analyte molecules in contact therewith. The phrase includes molecules used in MALDI, frequently referred to as "matrix", and explicitly includes cinnamic acid derivatives, sinapinic acid ("SPA"), cyano-hydroxy-cinnamic acid ("CHCA") and dihydroxybenzoic acid, ferulic acid, hydroxyacetophenone derivatives, as well as others. It also includes EAMs used in SELDI. In certain embodiments, the energy absorbing molecule is incorporated into a linear or cross-linked polymer, e.g., a polymethacrylate. For example, the composition can be a co-polymer of α-cyano-4-methacryloyloxycinnamic acid and acrylate. In another embodiment, the composition is a co-polymer of α-cyano-4-methacryloyloxycinnamic acid, acrylate and 3-(tri-methoxy)silyl propyl methacrylate. In another embodiment, the composition is a co-polymer comprising α-cyano-4-methacryloyloxycinnamic acid and octadecylmethacrylate ("C18 SEND"). SEND is further described in U.S. Pat. No. 5,719,060 and WO 03/64594 (Kitagawa, "Monomers And Polymers Having Energy Absorbing Moieties Of Use In Desorption/Ionization Of Analytes", Aug. 7, 2003).

SEAC/SEND is a version of SELDI in which both a binding moiety and an energy absorbing molecule are attached to the sample presenting surface. SEAC/SEND probes therefore allow the capture of analytes through affinity capture and desorption without the need to apply external matrix. The C18 SEND biochip is a version of SEAC/SEND, comprising a C18 moiety which functions as a binding moiety, and a CHCA moiety which functions as an energy absorbing moiety.

Protein biochips produced by Ciphergen Biosystems comprise surfaces having chromatographic or biospecific adsorbents attached thereto at addressable locations. Ciphergen ProteinChip® arrays include NP20, H4, H50, SAX-2, Q10, WCX-2, CM10, IMAC-30, LSAX-30, LWCX-30, IMAC-40, PS-10 and PS-20. These protein biochips comprise an aluminum substrate in the form of a strip. The surface of the strip is coated with silicon dioxide.

In the case of the NP-20 biochip, silicon oxide functions as a hydrophilic adsorbent to capture hydrophilic proteins.

H4, H50, SAX-2, WCX-2, IMAC-3, PS-10 and PS-20 biochips further comprise a functionalized, cross-linked polymer in the form of a hydrogel physically attached to the surface of the biochip or covalently attached through a silane to the surface of the biochip. The H4 biochip has isopropyl functionalities for hydrophobic binding. The H50 biochip has nonylphenoxy-poly(ethylene glycol) methacrylate for hydrophobic binding. The SAX-2 biochip has quarternary ammonium functionalities for anion exchange. The WCX-2 biochip has carboxylate functionalities for cation exchange. The IMAC-3 biochip has copper ions immobilized through nitrilotriacetic acid or IDA for coordinate covalent bonding. The PS-10 biochip has acyl-imidizole functional groups that can react with groups on proteins for covalent binding. The PS-20 biochip has epoxide functional groups for covalent binding with proteins. The PS-series biochips are useful for binding biospecific adsorbents, such as antibodies, receptors, lectins, heparin, Protein A, biotin/streptavidin and the like, to chip surfaces where they function to specifically capture analytes from a sample. The LSAX-30 (anion exchange), LWCX-30 (cation exchange) and IMAC-40 (metal chelate) biochips have functionalized latex beads on their surfaces. Such biochips are further described in: WO 00/66265 (Rich et al. ("Probes for a Gas Phase Ion Spectrometer," Nov. 9, 2000); WO 00/67293 (Beecher et al., "Sample Holder with Hydrophobic Coating for Gas Phase Mass Spectrometer," Nov. 9, 2000); U.S. patent application Ser. No. 09/908,518 (Pohl et al., "Latex Based Adsorbent Chip," Jul. 16, 2002) and U.S. patent application 60/350,110 (Um et al., "Hydrophobic Surface Chip," Nov. 8, 2001).

"Gas phase ion spectrometer" refers to an apparatus that detects gas phase ions. Gas phase ion spectrometers include an ion source that supplies gas phase ions. Gas phase ion spectrometers include, for example, mass spectrometers, ion mobility spectrometers, and total ion current measuring devices. "Gas phase ion spectrometry" refers to the use of a gas phase ion spectrometer to detect gas phase ions.

"Mass spectrometer" refers to a gas phase ion spectrometer that measures a parameter that can be translated into mass-to-charge ratios of gas phase ions. Mass spectrometers generally include an ion source and a mass analyzer. Examples of mass spectrometers are time-of-flight, magnetic sector, quadrapole filter, ion trap, ion cyclotron resonance, electrostatic sector analyzer and hybrids of these. "Mass spectrometry" refers to the use of mass spectrometry to detect gas phase ions.

"Probe" or "mass spectrometer probe" in the context of this invention refers to a device that can be used to introduce ions derived from an analyte into a gas phase ion spectrometer, such as a mass spectrometer. A "probe" will generally comprise a solid substrate (either flexible or rigid) comprising a sample-presenting surface on which an analyte is presented to the source of ionizing energy. "SELDI probe" refers to a probe comprising an adsorbent (also called a "binding moiety") attached to the surface. "Adsorbent surface" refers to a surface to which an adsorbent is bound. "Chemically selective surface" refers to a surface to which is bound either an adsorbent or a reactive moiety that is capable of binding a binding moiety, e.g., through a reaction forming a covalent or coordinate covalent bond.

"SELDI MS probe" refers to a probe comprising an adsorbent attached to the surface.

"Variance" in the context of the present invention refers to the mathematical variance in the concentrations of analytes in a test sample. A reduction in variance is one that is statistically significant ($p>0.05$). In simplest terms, the variance is the square of the standard deviation of all analyte concentrations in a test sample that are detected by at least one detection method. A preferred detection method is mass spectroscopy, where the amount of a detectable analyte is the area beneath the mass peak identified by the detector.

"Wash buffer" refers to a solution that may be used to wash and remove unbound material from an adsorbent surface. Wash buffers typically include salts that may or may not buffer pH within a specified range, detergents and optionally may include other ingredients useful in removing adventitiously associated material from a surface or complex.

"Elution buffer" refers to a solution capable of dissociating a binding moiety and an associated analyte. In some circumstances, an elution buffer is capable of disrupting the interaction between subunits when the subunits are associated in a complex. As with wash buffers, elution buffers may include detergents, salt, organic solvents and the like used separately or as mixtures. Typically, these latter reagents are present at higher concentrations in an elution buffer than in a wash buffer making the elution buffer more disruptive to molecular interactions. This ability to disrupt molecular interactions is termed "stringency," with elution buffers having greater stringency that wash buffers.

DETAILED DESCRIPTION OF THE INVENTION

Figure 5:
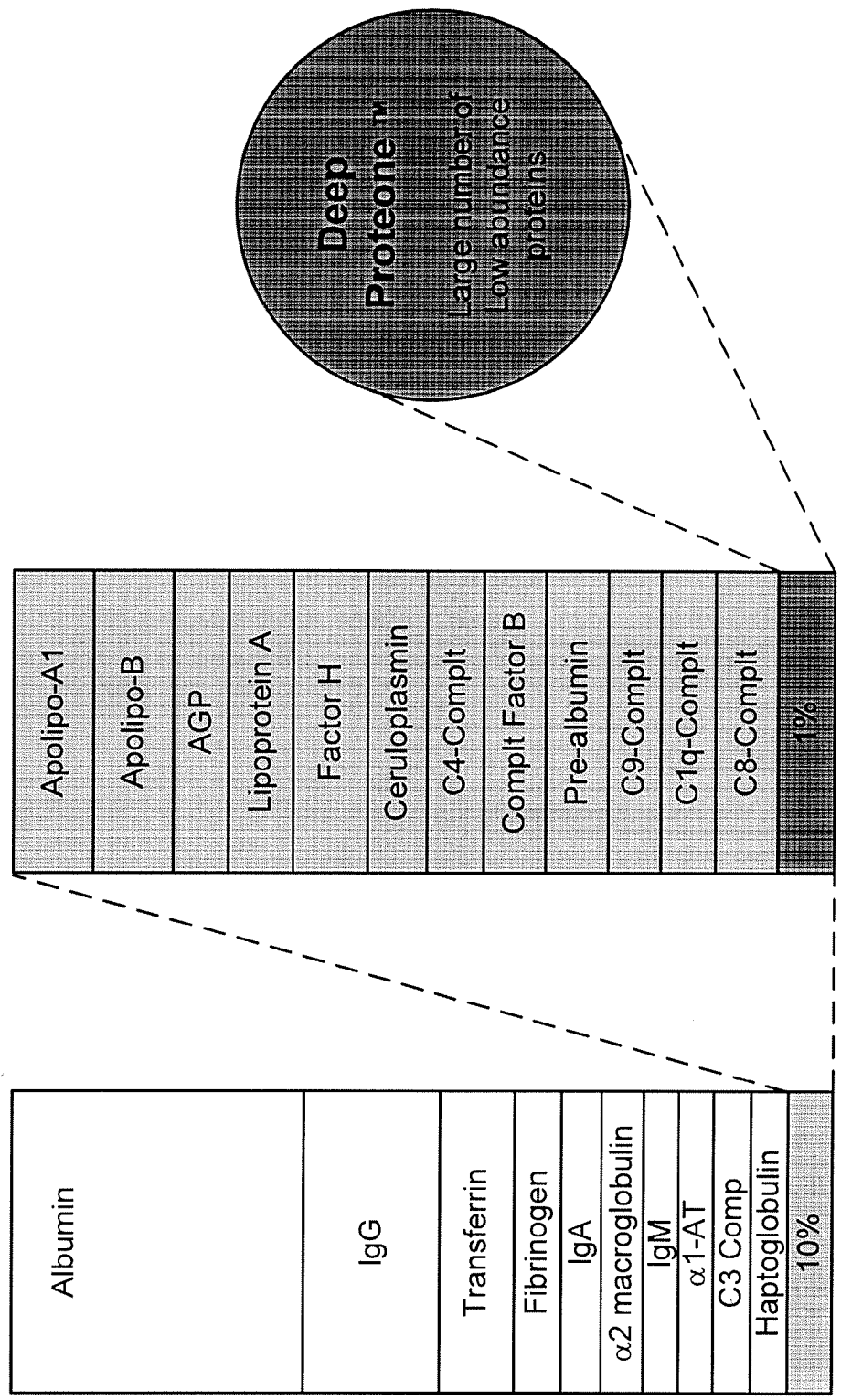
FIG. 5 is a graphical depiction of blood fractions (based on mass), highlighting the trace nature of a large number of low abundance proteins.

The present invention provides kits and methods that allow one of ordinary skill in the art to reduce the concentration range of analytes of interest found in a complex mixture. The methods described here have particular advantage over prior art methods using analyte specific reagents because they allow a reduction in the range of concentrations of analytes in samples that have unknown constituents and are complex in both number of different analytes present (greater than $10^3$) and in dynamic range of concentrations present (on the order of greater than $10^3$). Consequently, using the claimed invention allows simultaneous analysis of the "Deep Proteome,"

which consists of the large number of low abundance proteins present in many fluids from biological sources, including blood, plasma and serum. (See FIG. 5). The invention thus has utility in analytical preparation of complex mixtures of molecules, such as biological samples.

Reduction of the range of concentrations of analytes or concentration variance is accomplished by utilizing binding moiety libraries of defined size and diversity, preferably synthesized or coupled onto an inert support. When introduced to a solution containing a diversity of analytes, the binding moieties of the claimed invention will bind analytes of the solution. Abundant analytes will be present in amounts far in excess of the amount necessary to saturate the capacity of their respective binding moiety; therefore, a high percentage of the total amount of these abundant analytes will remain unbound. Conversely, the lesser amounts of the trace analytes means that these molecules will not saturate all of their available binding moieties; therefore, a greater percentage of the starting amount of the trace analytes will remain bound to their respective binding moieties as compared with the abundant analytes. Non-bound analytes may be removed by washing. When the bound analytes are eluted from the binding moieties there is a decreased relative amount of the abundant analytes in the eluted material relative to the starting material. In contrast, the amount of trace analytes is increased in the eluted material relative to the starting material. This coincident alteration of the relative concentrations of analytes results in an eluted material where many, if not all, analytes present in the solution can be detected in a single analysis, or in fewer analysis steps than would be the case with the starting material. In serum for example, albumins are abundant, many complement associated proteins, hormone-binding proteins are present in intermediate concentrations, while paracrine factors and cellular markers may be present at minute concentrations. Using the present invention, the range in analyte abundance observed in sera can be reduced, allowing many, if not most or even all analytes of interest to be analyzed.

Preparation of samples using the claimed invention is straightforward. After adsorbing the analytes of interest, the analytes are optionally washed to remove unbound analytes. Adsorbed analytes are then eluted from the binding moieties using, for example, by applying an elution buffer. The resulting solution contains all analytes of interest free from binding moieties; however, unlike the original complex mixture, the range in analyte concentration present in the resulting solution is relatively small as the concentration of high abundance analytes has been decreased and that of low abundance analytes increased relative to the original complex mixture. This modification in range of concentrations of analytes or concentration range between analytes allows for a larger percentage of the analytes in the resulting solution to be detected without the recalibration of the detection device necessary for direct analysis of complex mixtures having components present at widely different concentrations.

In some embodiments of the invention, analytes bound to binding moieties are eluted directly onto a probe or protein chip suitable for use in a mass spectrometer. To aid in analysis, elution buffers used in these embodiments may include a matrix material suitable for use in a mass spectrometer. Alternatively, the matrix material may be introduced to the analyte subsequent to deposition of the analyte on the probe or chip. In preferred embodiments of this type, SEND or SEAC/SEND biochips comprising a matrix material on the biochip are used. These preferred embodiments alleviate the need for a matrix material to be included in the elution buffer or introduced to the analyte at some point in time subsequent to deposition onto the biochip.

By providing a plurality of binding moieties, each recognizing a single or a low percentage of the analytes of interest present in a complex mixture, the present invention allows the composition of the complex mixture to be detected with minimal or no recalibration of the detection device. This includes detection of species that would otherwise not be detectable because either they were masked by high abundance analytes, or were present at too low a concentration to be detected by the method of analysis. This provides enormous benefits to high throughput analysis techniques that would otherwise be limited at the detection step by the need for multiple recalibrations, and/or multiple channels, and/or multiple detection steps or expensive and wasteful fractionation techniques necessitated by the large concentration range of the analytes present in many complex mixtures. Moreover, by increasing the relative concentration of low-abundance analytes, the invention allows detection of analytes that are only present in the sample in trace amounts. Using serum as an example, certain analytes such as some hormones are present at only trace amounts in unconcentrated sera. Other analytes, such as albumin, are abundant, being present in amounts ranging from micromolar to millimolar. The present invention concentrates the low abundance analytes relative to the high abundance analytes. Thus, in preparation of the exemplary serum sample using the present invention, the concentration of hormones is increased relative to the concentration of albumin and other high abundance analytes. By bringing the concentrations of low and high abundance analytes from the sera closer together, the analyte composition can be determined both qualitatively and quantitatively using only one or a few sensitivity settings of the analytical instrumentation used to detect the analytes.

By the same approach the present invention allows determining traces amount of proteins present in biological samples such as purified therapeutic proteins where the tolerance in protein impurity content is very limited. For examples purified antibodies from cell culture supernatants may contain traces of different proteins coming from the cells used for the expression of antibodies. These latter should not be present and are generally detected by specific ELISA assays. However when the concentration of impurities is very low immunochemical tests are not effective. If the sample to analyze is first treated according to the present invention protein impurity traces may be significantly concentrated and therefore detected by regular chemical or immunochemical methods.

I. Reducing Relative Analyte Concentrations in a Sample

A. Suitable Test Samples

Test samples of the present invention may be in any form that allows analytes present in the test sample to be contacted with binding moieties of the present invention, as described herein. Suitable test samples include gases, powders, liquids, suspensions, emulsions, permeable or pulverized solids, and the like. Preferably test solutions are liquids. Test samples may be taken directly from a source and used in the methods of the present invention without any preliminary manipulation. For example, a water sample may be taken directly from an aquifer and treated directly using the methods described herein.

Alternatively, the original sample may be prepared in a variety of ways to enhance its suitability for testing. Such sample preparations include depletion of certain analytes, concentrating, grinding, extracting, percolating and the like. For example, solid samples may be pulverized to a powder, then extracted using an aqueous or organic solvent. The extract from the powder may then be subjected to the methods of the present invention. Gaseous samples may be bubbled or percolated through a solution to dissolve and/or concentrate components of the gas in a liquid prior to subjecting the liquid to methods of the present invention.

Test samples preferably contain at least four analytes of interest, more preferably at least 8, 15, 20, 50, 100, 1000, 100,000, 1,000,000, 10,000,000 or more analytes of interest. In some circumstances, test samples suitable for manipulation using the methods of the present invention may include hundreds or thousands of analytes of interest. Preferably, the concentrations of analytes present in the test sample spans at least an order of magnitude, more preferably at least two, three, four or more orders of magnitude. Once subjected to the methods of the present invention, this concentration range for analytes detectable by at least one detection method will be decreased by at least a factor of two, more preferably a factor of 10, 20, 50, 100, 1000 or more.

Test samples may be collected using any suitable method. For example, environmental samples may be collected by dipping, picking, scooping, sucking, or trapping. Biological samples may be collected by swabbing, scraping, withdrawing surgically or with a hypodermic needle, and the like. The collection method in each instance is highly dependent upon the sample source and the situation, with many alternative suitable techniques of collection well-known to those of skill in the art.

1. Biological Test Samples

Test samples may be taken from any source that potentially includes analytes of interest including environmental samples such as air, water, dirt, extracts and the like. A preferred test sample of the present is a biological sample, preferably a biological fluid. Biological samples that can be manipulated with the present invention include amniotic fluid, blood, cerebrospinal fluid, intraarticular fluid, intraocular fluid, lymphatic fluid, milk, perspiration plasma, saliva semen, seminal plasma, serum, sputum, synovial fluid, tears, umbilical cord fluid, urine, biopsy homogenate, cell culture fluid, cell extracts, cell homogenate, conditioned medium, fermentation broth, tissue homogenate and derivatives of these. Analytes of interest in biological samples include proteins, lipids, nucleic acids and polysaccharides. More particularly, analytes of interest are cellular metabolites that are normally present in the animal, or are associated with a disease or infectious state such as a cancer, a viral infection, a parasitic infection, a bacterial infection and the like. Particularly interesting analytes are those that are markers for cellular stress. Analytes indicating that the animal is under stress are an early indicator of a number of disease states, including certain mental illnesses, myocardial infarction and infection.

Analytes of interest also include those that are foreign to the animal, but found in tissue(s) of the animal. Particularly interesting analytes in this regard include therapeutic drugs including antibiotics, many of which exist as different enantiomers and toxins that may be produced by infecting organisms, or sequestered in an animal from the environment. Samples can be, for example, egg white or *E. coli* extracts.

2. Environmental Test Samples

Environmental samples are another class of preferred test samples for use with the present invention. Preferred environmental samples include dirt, dust, dander, natural and synthetic fibers, water, plant materials, animal feces and the like. Preferred analytes in environmental samples include natural and synthetic toxins, fertilizers, herbicides and insecticides, and markers for bacterial and viral agents such as structural proteins characteristic of the agent of interest. Particularly preferred analytes sought in environmental test samples are toxins, particularly toxins such as botulinum, ricin, anthrax toxins and the like. Disease-related analytes of interest present in environmental test samples include complete virions as well as characteristic proteins and nucleic acids of botulinus, ebola, HIV, SARS, anthrax, plague, malaria, small pox, prions associated with bovine spongiform encephalopathy, scrapie, variant CJD etc.

Exemplary environmental samples can be obtained from numerous sources including the natural environment, such as a naturally-occurring body of water. The naturally-occurring body of water can be, for example, an ocean, a lake, a sea, a river, a swamp, a pond, a delta, or a bay. The environmental extract can alternatively be an extract from a water treatment center.

Alternatively, the environmental sample can be taken from a man-made environment, such as a building. The building can be any man-made building. Preferably, the building is contaminated with one or more biological pathogens such as small pox, anthrax, or one or more toxic agents, such as sarin, soman, nerve poisons, explosive chemicals, pesticides, VX, and blister agents. Methods for obtaining the environmental sample include dry swabbing the surface of the building, or wet swabbing the building's surface using a suitable solvent known to those of skill in the art.

B. Suitable Binding Moieties

Suitable binding moieties of the present invention include small organic molecules, such as dyes and tryazines, and biopolymers such as peptides, proteins, polynucleotides, oligosaccharides or lipids. Binding moieties of the present invention may be molecules having molecular weights of 100 KDa or more, such as antibodies, but preferably are smaller molecules with a molecular weight in the range of 10 KDa, more preferably around 1 KDa, desirably less than 1 KDa for example, less than 750, 500, or 250 Da. Ideally, binding moieties of the present invention are coupled to an insoluble particulate material. Each insoluble particle preferably carries several copies of the same binding moiety, with each particle type coupling a different binding moiety.

Binding moieties of the present invention may be in solution, suspension, or in any other situation allowing contact of the binding moiety with analyte including mounted on a solid support.

The binding moieties may be part of a "phage display library" where the peptide is presented as part of the phage coat. (See, e.g., Tang, Xiao-Bo, et al.; J. Biochem; 1997; pp. 686-690; vol. 122, No. 4). Presenting the peptide on the surface of the phage particle allows rapid throughput screening of combinatorial libraries of small peptides, a method that is also advantageous for screening combinatorial antibody libraries. A phage display library is formed from bacteriophage that has been recombinantly manipulated to express binding moiety as part of the phage protein coat. Using phage display, libraries of binding moieties may be easily constructed.

Binding moieties may also be soluble combinatorial molecules. Soluble combinatorial molecules preferably comprise a capture moiety that allows the binding moiety to be coupled to a complementary solid support. Soluble binding moiety embodiments are typically contacted to the sample and allowed to bind analyte(s) of interest prior to isolating the resulting complexes by binding or coupling the binding moiety to a solid support. Combinatorial libraries may be composed of building blocks containing chiral atoms such as 19 of the naturally occurring amino acids.

Binding moieties of the present invention may be produced using any technique known to those of skill in the art. For example, binding moieties may be chemically synthesized, harvested from a natural source or, in the case of binding moieties that are bio-organic polymers, produced using recombinant techniques. For this latter reason, peptides having no more than 15, 10, 8, 6 or 4 amino acids are particularly advantageous, as they are easily produced using recombinant or solid phase chemistry techniques. Moreover, chemically synthesized libraries are described, for example, in Fodor et al., Science 251: 767-773 (1991) and Houghten et al., Nature 354: 84-86 (1991). In the split-couple-recombine solid phase combinatorial synthesis Lam et al., Nature 354, 82-84 (1991) such that the diversity of the complement of binding moieties is a result of the number of different amino acids to the power of the length of the binding moiety (number of amino acids in an individual binding moiety).

Nucleic acids are another preferred bio-organic polymer binding moiety. As with peptides, nucleic acids may be produced using synthetic or recombinant techniques well-known to those of skill in the art. Preferable nucleic acid binding moieties of the present invention are at least 4, more preferably 6, 8, 10, 15, or 20 nucleotides in length. Nucleic acid binding moieties include single or double stranded DNA or RNA molecules (e.g., aptamers) that bind to specific molecular targets, such as a protein or metabolite.

Oligosaccharide binding moieties are also contemplated as part of the invention. Oligosaccharide binding moieties are preferably at least 5 monosaccharide units in length, more preferably 8, 10, 15, 20, 25 or more monosaccharide units in length.

A biopolymer binding moiety can be a lipid. As used herein, the term "lipid" refers to a hydrophobic or amphipathic moiety. Thus, lipid library of binding moieties are also contemplated for use in the methods and kits of the invention. Suitable lipids include a C14 to C50 aliphatic, aryl, arylalkyl, arylalkenyl, or arylalkynyl moiety, which may include at least one heteroatom selected from the group consisting of nitrogen, sulfur, oxygen, and phosphorus. Other suitable lipids include a phosphoglyceride, a glycosylglyceride, a sphingolipid, a sterol, a phosphatidyl ethanolamine or a phosphatidyl propanolamine. Lipid library of binding moieties are preferably at least 5 units in length, more preferably at least 8, 10, 15, 20, 25, 50 or more units in length.

Small organic molecules are also contemplated as binding moieties of the present invention. Typically, such molecules have properties that allow for ionic, hydrophobic or affinity interaction with the analyte. Small organic binding moieties include chemical groups traditionally used in chromatographic processes such as mono-, di- and tri-methyl amino ethyl groups, mono-, di- and tri-ethyl amino ethyl groups, sulphonyl, phosphoryl, phenyl, carboxymethyl groups and the like. For example libraries may use benzodiazepines, (see, e.g. Bunin et al., Proc. Natl. Acad. Sci. USA 91: 4708-4712 (1994)) and peptoids (e.g. Simon et al., Proc. Natl. Acad. Sci. USA 89: 9367-9371 (1992)). In another embodiment, the binding moiety is a dye or a triazine derivative. This list is by no means exhaustive, as one of skill in the art will readily recognize thousands of chemical functional groups with ionic, hydrophobic or affinity properties compatible with use as binding moieties of the present invention. The production and use of combinatorial binding moiety libraries is discussed in more detail, below.

Binding moieties may be purchased pre-coupled to the supports, synthesized on the support, or may be indirectly attached or directly immobilized on the support using standard methods (see, for example, Harlow and Lane, *Antibodies*, Cold Spring Harbor Laboratory, Cold Spring Harbor, N.Y. (1988); Biancala et al., *Letters in Peptide Science* 7(291): 297 (2000); MacBeath et al., *Science* 289: 1760-1763 (2000); Cass et al., ed., *Proceedings of the Thirteenth American Peptide Symposium*; Leiden, Escom, 975-979 (1994); U.S. Pat. No. 5,576,220; Cook et al., *Tetrahedron Letters* 35: 6777-6780 (1994); and Fodor et al., *Science* 251(4995): 767-773 (1991)).

Combinatorial Libraries

In one embodiment of this invention the library of binding moieties is a combinatorial library or portion thereof. A combinatorial chemical library is a collection of compounds generated by either chemical synthesis or biological synthesis, by combining a number of chemical "building blocks" in all possible combinations. For example, a complete linear combinatorial chemical library, such as a polypeptide library, is formed by combining a set of chemical building blocks (amino acids) in every possible way for a given compound length (i.e., the number of amino acids in a polypeptide compound). As an example, if the number of building blocks is 5 and the construct is composed of five members, the number of possible linear combinations is of $5^5$ or 3,125 members. In this case the building blocks (A, B, C, D and E) are assembled linearly such as: A-A-A-A-A; A-A-A-A-B; A-A-A-A-C; A-A-A-B-A; A-A-A-B-B; A-A-A-B-C; . . . ; A-A-B-A-A; A-A-B-A-B; A-A-B-A-C; . . . ; E-E-E-E-C; E-E-E-E-D; E-E-E-E-E.

Another form of combinatorial library is scaffold-based. These constructs are based of a single central molecule or core, comprising positions that can be substituted by building blocks. An example is given by trichloro-triazine (three substitutable positions) on which several substituents can be attached. If the number of substituents is three, the number of possible combinations is 10. It is also possible to consider the relative positioning of each substituent; in this case the number of combinations is larger.

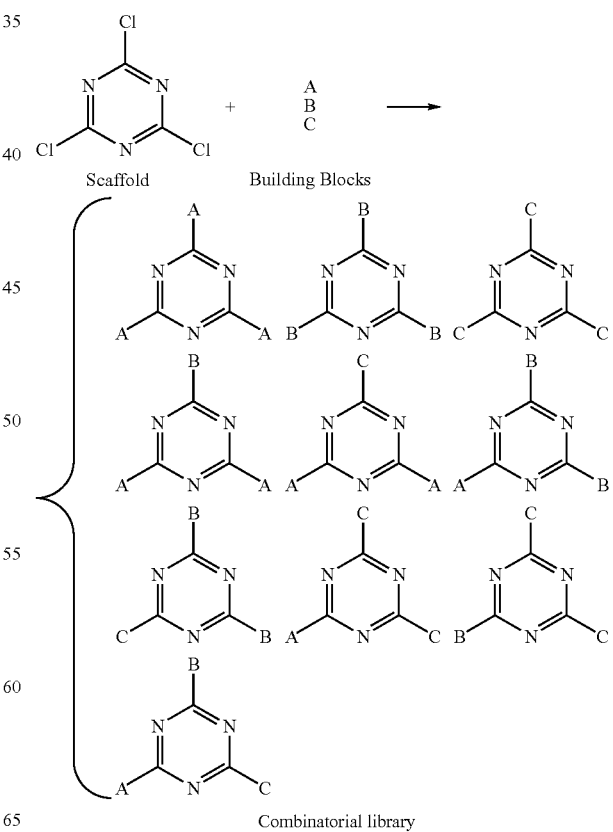

Combinatorial library

As a third level it is possible to combine linear combinatorial libraries with scaffold-based libraries where substituents of this latter are combinatorial linear sequences.

Millions of chemical compounds can be synthesized through such combinatorial mixing of chemical building blocks. For peptide binding moieties, the length is preferably limited to 15, 10, 8, 6 or 4 amino acids. Nucleic acid binding moieties of the invention have preferred lengths of at least 4, more preferably 6, 8, 10, 15, or at least 20 nucleotides. Oligosaccharides are preferably at least 5 monosaccharide units in length, more preferably 8, 10, 15, 20, 25 or more monosaccharide units.

Combinatorial libraries may be complete or incomplete. Complete combinatorial libraries of biopolymers are those libraries containing a representative of every possible permutation of monomers for a given polymer length and composition. Incomplete libraries are those libraries lacking one or more possible permutation of monomers for a given polymer length.

Peptide binding moieties are a preferred embodiment of the claimed invention. Methods for generating libraries of peptide binding moieties suitable for use in the claimed invention are well known to those of skill in the art, e.g., the "split, couple, and recombine" method (see, e.g., Furka et al., Int. J. Peptide Protein Res., 37: 487493 (1991); Houghton et al., Nature 354:84-88 (1991); Lam et al., Nature, 354: 82-84 (1991); International Patent Application WO 92/00091; and U.S. Pat. Nos. 5,010,175, 5,133,866, and 5,498,538) or other approaches known in the art. The expression of peptide libraries also is described in Devlin et al., Science, 249: 404-406 (1990).

Combinatorial and synthetic chemistry techniques well-known in the art can generate libraries containing millions of members (Lam et al., Nature 354: 82-84 (1991) and International (PCT) Patent Application WO 92/00091), each having a unique structure. A library of linear hexamer ligands made with 18 of the natural amino acids, for example, contains $34 \times 10^6$ different structures. When amino acid analogs and isomers are also included, the number of potential structures is practically limitless. Moreover, each member of such a library potentially possesses the capacity to bind to a different molecule. Members of a combinatorial library can be synthesized on or coupled to a solid support, such as a bead, with each bead essentially having millions of copies of a library member on its surface. As different beads may be coupled to different library members and the total number of beads used to couple the library members large, the potential number of different molecules capable of binding to the bead-coupled library members is enormous.

Hammond et al., US 2003/0212253 (Nov. 13, 2003) describes combinatorial libraries along the following lines. Peptide binding moiety libraries may be synthesized from amino acids that provide increased stability relative to the natural amino acids. For example, cysteine, methionine and tryptophan may be omitted from the library and unnatural amino acids such as 2-naphylalanine and norleucine included. The N-terminal amino acid may be a D-isomer or may be acetylated to provide greater biochemical stability in the presence of amino-peptidases. The binding moiety density must be sufficient to provide sufficient binding for the target molecule, but not so high that the binding moieties interact with themselves rather than the target molecule. A binding moiety density of 0.1 μmole-500 μmole per gram of dry weight of support is desired and more preferably a binding moiety density of 10 μmole-100 μmole per gram of support is desired. A 6-mer peptide library was synthesized onto Toyopearl-AF Amino 650M resin (Tosohaas, Montgomeryville, Pa.). The size of the resin beads ranged from 60-130 mm per bead. Initial substitution of the starting resin was achieved by coupling of a mixture of Fmoc-Ala-OH and Boc-Ala-OH (1:3.8 molar ratio). After coupling, the Boc protecting group was removed with neat TFA in full. The resulting deprotected amino groups were then acetylated. Peptide chains were assembled via the remaining Fmoc-Ala-OH sites on the resin bead. Standard Fmoc synthetic strategies were employed. In one embodiment a typical experiment, six grams of Fmoc-Ala-(Ac-Ala-) Toyopearl Resin was deprotected with 20% piperdine/DMF (2×20 min), then washed with DMF (8 times) and equally divided into 18 separate reaction vessels. In each separate vessel, a single Fmoc-amino acid was coupled to the resin (BOP/NMM, 5-10 told excess) for 4-7 hours. The individual resins were washed and combined using the "split/mix" library technique (Furka et al., Int. J. Peptide Protein Res., 37, 487-493 (1991); Lam et al., Nature, 354, 82-84 (1991); International Patent Application WO 92/00091 (1992); U.S. Pat. Nos. 5,010,175; 5,133, 866; and 5,498,538). The cycle of deprotection and coupling was repeated until the amino acid sequence was completed (six cycles for a hexamer library). The final Fmoc was removed from peptide resins using 20% piperidine/DMF in separate reaction vessels during the last coupling cycle. Side-chain protecting groups were removed with TFA treatment (TFA:H.sub.20:Phenol, 90:5:5) for 2 hours. Resins were washed extensively and dried under a vacuum. Peptide densities achieved were typically in the range of 0.06-0.12 mmol/g of resin. The amino acids may be either L or D-stereoisomers or racemates.

Sequencing and peptide composition of peptide ligand-resin bead complexes were confirmed, and the degree of substitution of the resin was calculated by quantitative amino acid analysis at Commonwealth Biotechnologies, Inc., Richmond, Va. Sequencing was performed at Protein Technologies Laboratories, Texas A&M University, by Edman degradation using a Hewlett Packard G1005A.

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

In some peptide library embodiments, the peptides are expressed on the surface of recombinant bacteriophage to produce large, easily screened, libraries. Using the "phage method" (Scott and Smith, Science 249:386-390, 1990; Cwirla, et al, Proc. Natl. Acad. Sci., 87:6378-6382, 1990; Devlin et al., Science, 49:404-406, 1990), very large libraries can be constructed ($10^6$-$10^8$ chemical entities). A second approach uses primarily chemical methods, of which the Geysen method (Geysen et al., Molecular Immunology 23:709-715, 1986; Geysen et al. J. Immunologic Method 102: 259-274, 1987; and the method of Fodor et al. (Science 251: 767-773, 1991) are examples. Furka et al. (14th International Congress of Biochemistry, Volume #5, Abstract FR:013, 1988; Furka, Int. J. Peptide Protein Res. 37:487-493, 1991), Houghton (U.S. Pat. No. 4,631,211, issued December 1986) and Rutter et al. (U.S. Pat. No. 5,010,175, issued Apr. 23, 1991) describe methods to produce a mixture of peptides that can be tested as agonists or antagonists.

Other chemistries for generating chemical diversity libraries can also be used. Such chemistries include, but are not limited to: peptides (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288, 514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science*, 274:1520-1522 (1996) and U.S. Pat. No. 5,593,853), small organic molecule libraries (see, e.g., benzodiazepines, Baum C&EN, Jan. 18, page 33 (1993); isoprenoids, U.S. Pat. No. 5,569,588; thiazolidinones and metathiazanones, U.S. Pat. No. 5,549, 974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Linker Moieties

Binding moieties of the present invention optionally include linker moieties that allow targeted and/or reversible coupling of the binding moiety to a solid support. Exemplary linker moieties include epitope and his-tags, which are attached to the biomolecule to be captured to form a fusion protein. In these instances, a cleavable linker sequence, such as those specific for Factor XA or enterokinase (Invitrogen, San Diego, Calif.) may be optionally included between the biomolecule and the capture moiety to facilitate isolation and/or separation of the components of the fusion molecule. Protein domains specifically recognized by designer ligands may also be used as linker moieties (See, e.g., Deisenhofer, J., Biochemistry 20 (1981) 2361-2370). Many other equivalent linker moieties are known in the art. See, e.g., Hochuli, *Chemische Industrie*, 12:69-70 (1989); Hochuli, *Genetic Engineering, Principle and Methods*, 12:87-98 (1990), Plenum Press, N.Y.; and Crowe, et al. (1992) *OIAexpress: The High Level Expression & Protein Purification System*, QIAGEN, Inc. Chatsworth, Calif.; which are incorporated herein by reference. Antigenic determinants and other characteristic properties of the biomolecule to be adsorbed may also serve as capture moiety tags. Exemplary linker moieties include poly-histidine (poly-his) or poly-histidine-glycine (poly-his-gly) tags; the flu HA tag polypeptide and its antibody 12CA5 [Field et al., Mol. Cell. Biol., 8:2159-2165 (1988)]; the c-myc tag and the 8F9, 3C7, 6E10, G4, B7 and 9E10 antibodies thereto (Evan et al., Molecular and Cellular Biology, 5:3610-3616 (1985)); and the Herpes Simplex virus glycoprotein D (gD) tag and its antibody (Paborsky et al., Protein Engineering, 3(6):547-553 (1990)). Other tag polypeptides include the Flag-peptide (Hopp et al., BioTechnology, 6:1204-1210 (1988)); the KT3 epitope peptide (Martin et al., *Science*, 255:192-194 (1992)); a α-tubulin epitope peptide (Skinner et al., J. Biol. Chem., 266: 15163-15166 (1991)); and the T7 gene 10 protein peptide tag (Lutz-Freyermuth et al., Proc. Natl. Acad. Sci. USA, 87: 6393-6397 (1990)).

C. Capturing Analytes From A Test Sample Using Binding Moieties

Analytes present in a test sample are captured by contacting the test sample with the binding moieties under conditions that allow each binding moiety to couple with its corresponding analyte. As inferred above, binding moieties may be contacted with the test sample directly, or the binding moieties may be first attached to a solid support, such as a dipstick, SELDI probe, or insoluble polymeric bead, membrane or powder.

In the case in which the binding moieties are part of a bead library, the ratio of bead volume to sample volume for a complex sample such as serum can be between, for example, 1:150 and 1:1. The smaller the ratio of beads to sample, the greater the ability to increase the relative concentration of low abundance or rare analyte species. At a constant bead:sample volume of 1:10, volumes of beads used with serum can be at least between 0.0005 ml and 15 mL of beads (including 0.020 ml).

In one embodiment, the binding moiety is coupled to a solid support prior to contacting the test sample. In this alternative embodiment, the solid support is simply contacted with the test sample for a time sufficient to allow the binding moiety to bind analyte, then the solid support is withdrawn from the test sample with the analyte bound to it via formation of a complex between the analyte and the binding moiety.

In one embodiment, the binding moieties include a linker moiety. In this embodiment the binding moieties are contacted directly to the test sample in a manner that allows analytes present in the test sample to bind to the binding moieties. After sufficient time has elapsed, a solid support that includes a complementary capture moiety to the capture moiety of the binding moiety is contacted to the test sample. This allows the binding moiety to couple with the solid support through the capture moiety, while retaining the bound analyte.

Contacting the binding moiety with the test sample may be accomplished by admixing the two, swabbing the test sample onto the binding moiety, flowing the test sample over the solid support having binding moieties attached thereto, and other methods that would be obvious to those of ordinary skill in the art. The binding moieties and the analytes are kept in contact for a time sufficient to allow the binding moieties to reach binding equilibrium with the sample. Under typical laboratory conditions this is at least 10 minutes.

Solid Supports

Acceptable supports for use in the present invention can vary widely. A support can be porous or nonporous. It can be continuous or non-continuous, flexible or nonflexible. A support can be made of a variety of materials including ceramic, glassy, metallic, organic polymeric materials, or combinations thereof.

Preferred supports include organic polymeric supports, such as particulate or beaded supports, woven and nonwoven webs (such as fibrous webs), microporous fibers, microporous membranes, hollow fibers or tubes. Polyacrylamide and mineral supports such as silicates and carbonates (e.g., hydroxyl apatite) can also be used. Woven and nonwoven webs may have either regular or irregular physical configurations of surfaces. Particularly preferred embodiments include solid supports in the form of spherical or irregularly-shaped beads or particles.

Porous materials are useful because they provide large surface areas. The porous support can be synthetic or natural, organic or inorganic. Suitable solids with a porous structure having pores of a diameter of at least about 1.0 nanometer (nm) and a pore volume of at least about 0.1 cubic centimeter/ gram ($cm^3/g$). Preferably, the pore diameter is at least about 30 nm because larger pores will be less restrictive to diffusion. Preferably, the pore volume is at least about 0.5 $cm^3/g$ for greater potential capacity due to greater surface area surrounding the pores. Preferred porous supports include particulate or beaded supports such as agarose, hydrophilic polyacrylates, polystyrene, mineral oxides and Sepharose, including spherical and irregular-shaped beads and particles.

For significant advantage, the supports for binding moieties are preferably hydrophilic. Preferably, the hydrophilic polymers are water swellable to allow for greater infiltration of analytes. Examples of such supports include natural polysaccharides such as cellulose, modified celluloses, agarose, cross-linked dextrans, amino-modified cross-linked dextrans, guar gums, modified guar gums, xanthan gums, locust bean gums and hydrogels. Other examples include cross-linked synthetic hydrophilic polymers such as polyacrylamide, polyacrylates, polyvinyl alcohol (PVA) and modified polyethylene glycols.

Attachment of the binding moieties to the solid support may be accomplished through a variety of mechanisms. The solid support can be derivatized with a fully prepared binding moiety by attaching a previously prepared binding moiety to the solid support. Alternatively, the binding moiety may be formed on the solid support by attaching a precursor molecule to the solid support and subsequently adding additional precursor molecules to the growing chain bound to the solid support by the first precursor molecule. This mechanism of building the adsorbent on the solid support is particularly useful when the binding moiety is a polymer, particularly a biopolymer such as a polypeptide, polynucleotide or polysaccharide molecule. A biopolymer adsorbent can be provided by successively adding monomeric components (e.g., amino acids, nucleotides or simple sugars) to a first monomeric component attached to the solid support using methods known in the art. See, e.g., U.S. Pat. No. 5,445,934 (Fodor et al.).

In certain embodiments, for example combinatorial libraries, each solid support, e.g., each bead, can have only one binding moiety attached to it (within the limits of combinatorial chemistry).

However, in another embodiment, each solid support can have a plurality of different binding moieties attached. For example, a combinatorial library of peptides can be manufactured using the split-and-pool process. These peptides can be cleaved from the beads to which they attached, mixed, and then attached to a new set of beads, without any sorting of the peptides by beads. In this way, each bead will have many different binding moieties attached. Accordingly, this invention provides combinatorial libraries of binding moieties in which a plurality of different members of the combinatorial library are attached to the same solid support. As few as one and as many as 10, 100, 1000, 10,000, 1,000,000, 1,000,000,000 or more different binding moieties may be coupled to a single solid support. In certain embodiments the solid support is in the form of beads, with a single, different, binding moiety type bound to each bead. For example in a peptide binding moiety library, peptides representing one possible permutation of amino acids would be bound to one bead, peptides representing another possible permutation to another bead, and so on.

Binding moieties may be coupled to a solid support using reversible or non-reversible interactions. For example, non-reversible interactions may be made using a support that includes at least one reactive functional group, such as a hydroxyl, carboxyl, sulfhydryl, or amino group that chemically binds to the binding moiety, optionally through a spacer group. Suitable functional groups include N-hydroxysuccinimide esters, sulfonyl esters, iodoacetyl groups, aldehydes, epoxy, imidazolyl carbamates, and cyanogen bromide and other halogen-activated supports. Such functional groups can be provided to a support by a variety of known techniques. For example, a glass surface can be derivatized with aminopropyl triethoxysilane in a known manner. In some embodiments, binding moieties are coupled to a solid support during synthesis, as is known to those of skill in the art (e.g., solid phase peptide and nucleic acid synthesis).

Alternatively, reversible interactions between a solid support and a binding moiety may be made using linker moieties associated with the solid support and/or the binding moiety. A variety of linker moieties suitable for use with the present invention are known, some of which are discussed above. Use of linker moieties for coupling diverse agents is well known to one of ordinary skill in the art, who can apply this common knowledge to form solid support/binding moiety couplings suitable for use in the present invention with no more that routine experimentation.

Microparticulate Solid Supports

A preferred embodiment of the present invention utilizes small, beaded, microparticulate solid supports that are less than 1000 μm, preferably less than 100, 10, 1 or 0.1 μm in diameter. Such supports are typically formed by mechanical milling or otherwise reducing larger beads to a powder consistency. Microparticulate solid supports are desirable because they possess increased surface area to volume ratio compared to the larger bead. Microparticulate solid supports also decrease the volume of support necessary to contain a combinatorial library of the invention, thereby allowing more complex and efficient libraries to be used. Using existing equipment however, it is difficult to synthesize combinatorial libraries on very small (<10 μm) beads due to the limitations in frit sizes of the filter systems used. To overcome this problem the combinatorial library may be synthesized in bulk on a beat that may then be fragmented by mechanically grinding, crushing, or sonicating it to form a powder or collection of micro-particles.

Using these techniques, microparticulate solid supports coupled to different binding moieties may be produced. These in turn may be extensively mixed to form a more uniform composition relative to mixing larger or various sizes of different beads.

The microparticulate solid support may be covalently attached to an activated surface to make a "dipstick" or chip through an epoxy group, N-hydroxysuccinimide, dimethyl 3,3'-dithiopropionimidate, or glutaraldehyde so as to form a chemical bond with the ligands of the combinatorial library or with the base matrix of the polymer on which the ligands were synthesized. This may be achieved through cross-linking to the N-terminal amino group of a peptide library.

Non-reacted cross-linking groups on the surface may be reacted with a small chemical such a mercapto-ethanol to prevent further reactivity. In addition, surfaces may be further treated to prevent non-specific adhesion of protein.

Target molecules bound to binding moieties coupled to microparticulate solid supports may be washed in one or a variety of ways, e.g. with buffer at different salt concentrations and pH and the bound proteins eluted in solutions of low pH, low or high ionic strength, strong chaotropes, acetonitrile/formic acid, etc.

Eluted target molecules may be analyzed for protein composition according to molecular weight by several methods, including, but not limited to, for example, mass spectrometry, SDS-PAGE, capillary electrophoresis, or by pI through isoelectric focusing.

Alternatively, target molecules may be eluted through electrophoresis. In this embodiment the microparticulate solid supports containing bound target molecules may be soaked with an appropriate solution such as Laemmli buffer and the proteins resolved by SDS-PAGE analysis. An alternative buffer may contain urea and the proteins may be separated by electrophoresis into an isoelectric focusing gel Alternatively, the microparticulate solid supports may be compounded with a bulking agent and compacted into tablet form. In this format it may be added directly to a sample solution or instead, first suspended in buffer.

Microparticulate solid supports may be placed into solution such as agarose or acrylamide and cross-linked into a gel itself or cross-linked to each other through a polymerization reaction with a cross-linker on a fiber to form a monolithic material.

Alternatively microparticulate solid supports may be immobilized onto a thin film of adhesive.

Another approach is the entrapment of microparticulate solid supports in a porous matrix. Such matrixes could include nonwoven fibers or webs with the particles possibly being incorporated during the melt blowing stage.

Microparticles can be incorporated into a single sheet or stack of membranes as desired to achieve the appropriate desired binding capacity; in which the microparticulate solid supports are entrapped between the layers by calendering or hydroentanglement.

The membrane composition can be selected from natural or synthetic sources including polyester and polypropylene fibers and meshes. Of course, one of skill in the art will be aware that many of the techniques described in this section are generally applicable to other embodiments of the present invention.

1. Removing Unbound Analytes

A feature of the present invention is that treatment of analytes according to the methods described herein preferably concentrates and partially purifies bound analyte in addition to reducing the variance between analyte concentrations. Implementation of this feature to the fullest includes optionally washing any unbound analytes from the analyte bound to the binding moieties on the solid support.

Washing away unbound analyte is preferably performed by contacting the analyte bound to the binding moiety with a mild wash solution. The mild wash solution is designed to remove contaminants and unbound analytes frequently found in the test sample originally containing the analyte. Typically a wash solution will be at a physiologic pH and ionic strength and the wash will be conducted under ambient conditions of temperature and pressure.

Formulation of wash solutions suitable for use in the present invention can be performed by one of skill in the art without undue experimentation. Methods for removing contaminants, including low stringency washing methods, are published, for example in Scopes, *Protein Purification: Principles and Practice* (1982); Ausubel, et al. (1987 and periodic supplements); *Current Protocols in Molecular Biology*; Deutscher (1990) "*Guide to Protein Purification*" in *Methods in Enzymology* vol. 182, and other volumes in this series.

D. Isolating Captured Analytes From Binding Moieties

Bound analyte may be eluted from the binding moieties and isolated using a variety of methods, preferably by using an aqueous elution buffer that disrupts the interaction between the binding moiety and the analyte. Any suitable elution buffer may be used for this purpose, including denaturing agents such as chaotropes and organic solvents. Exemplary elution buffers include aqueous salt solutions of very low or high ionic strength, detergent solutions, and organic solvents. Solutions and suspensions of agents that competitively bind to binding moieties of the invention my also be used in elution buffers, provide that such competitive binding agents do not interfere with subsequent collection or analysis of the analytes of interest. The elution buffer(s) chosen are highly application-specific and may be readily identified by one of ordinary skill in the art through materials commonly available in the public domain or through routine experimentation (See, e.g., Scopes, *Protein Purification: Principles and Practice* (1982); and Deutscher (1990) "*Guide to Protein Purification*" in *Methods in Enzymology* vol. 182, and other volumes in this series).

A typical sequence includes washing with sodium chloride (to collect proteins adsorbed by a dominant ion exchange interaction), followed by ethylene glycol (eluent for protein interacting mainly by hydrophobic associations), followed by lowering the pH to 2.5 (deforming buffer) and finally by guanidine-HCl.

Examples of suitable elution buffers include those that modify surface charge of an analyte and/or binding moiety, such as pH buffer solutions. pH buffer solutions used to disrupt surface charge through modification of acidity preferably are strong buffers, sufficient to maintain the pH of a solution in the acidic range, i.e., at a pH less than 7, preferably less than 6.8, 6.5, 6.0, 5.5, 5.0, 4.0 or 3.0; or in the basic range at a pH greater than 7, preferably greater than 7.5, 8.0, 8.3, 8.5, 9.0, 9.3, 10.0 or 11.0. In certain embodiments, the elution buffer can comprise 9 M urea at pH 3, 9 M urea at pH 11 or a mixture of 6.66% MeCN 13.33% IPA/79.2% H20/0.8% TFA. The selection of one method versus another depends on the analytical method used for the equalized sample.

Alternatively, solutions of high salt concentration having sufficient ionic strength to mask charge characteristics of the analyte and/or binding moiety may be used. Salts having multi-valent ions are particularly preferred in this regard, e.g., sulphates and phosphates with alkali earth or transition metal counterions, although salts dissociating to one or more monovalent are also suitable for use in the present invention, provided that the ionic strength of the resulting solution is at least 0.1, preferably 0.25, 0.3, 0.35, 0.4, 0.5, 0.75, 1.0 mol $l^{-1}$ or higher. By way of example, many protein analyte/binding moiety interactions are sensitive to alterations of the ionic strength of their environment. Therefore, analyte may be isolated from the binding moiety by contacting the bound analyte with a salt solution, preferably an inorganic salt solution such as sodium chloride. This may be accomplished using a variety of methods including bathing, soaking, or dipping a solid support to which the analyte is bound into the elution buffer, or by rinsing, spraying, or washing the elution buffer over the solid support. Such treatments will release the analyte from the binding moiety coupled to the solid support. The analyte may then be recovered from the elution buffer.

Chaotropic agents, such as guanidine and urea, disrupt the structure of the water envelope surrounding the binding moiety and the bound analyte, causing dissociation of complex between the analyte and binding moiety. Chaotropic salt solutions suitable for use as elution buffers of the present invention are application specific and can be formulated by one of skill in the art through routine experimentation. For example, a suitable chaotropic elution buffer may contain urea or guanidine ranging in concentration from 0.1 to 9 M.

Detergent-based elution buffers modify the selectivity of the affinity molecule with respect to surface tension and molecular complex structure. Suitable detergents for use as elution buffers include both ionic and nonionic detergents. Non-ionic detergents disrupt hydrophobic interactions between molecules by modifying the dielectric constant of a solution, whereas ionic detergents generally coat receptive molecules in a manner that imparts a uniform charge, causing the coated molecule to repel like-coated molecules. For example, the ionic detergent sodium dodecyl sulphate (SDS) coats proteins in a manner that imparts a uniform negative charge. Examples of non-ionic detergents include Triton X-100, TWEEN, NP-40 and Octyl-glycoside. Examples of zwitterionic detergents include CHAPS.

Another class of detergent-like compounds that disrupt hydrophobic interactions through modification of a solution's dielectric constant includes ethylene glycol, propylene glycol and organic solvents such as ethanol, propanol, acetonitrile, and glycerol.

A preferred elution buffer of the present invention includes a matrix material suitable for use in a mass spectrometer. A matrix material may be included in the elution buffer. Some embodiments of the invention may optionally include eluting analyte(s) from binding moieties directly to mass spectrometer probes, such as protein or biochips. In other embodiments of the invention the matrix may be mixed with analyte(s) after elution from binding moieties. Still other embodiments include eluting analytes directly to SEND or SEAC/SEND protein chips that include an energy absorbing matrix predisposed on the protein chip. In these latter embodiments, there is no need for additional matrix material to be present in the elution buffer.

Other elution buffers suitable for the present invention include combinations of buffer components mentioned above. Elution buffers formulated from two or more of the foregoing elution buffer components are capable of modifying the selectivity of molecular interaction between subunits of a complex based on multiple elution characteristics.

Analytes isolated using the present invention will have a range of concentrations of analytes or concentration variance between analytes that is less than the range of concentrations of analytes or concentration variance originally present in the test sample. For example, after manipulation using the methods of the present invention, isolated analytes with have a range of concentrations of analytes or concentration variance from other isolated analytes that is decreased by at least a factor of two, more preferably a factor of 10, 20, 25, 50, 100, 1000 or more, from the concentration variance between the same analytes present in the test sample prior to subjecting the test sample to any of the methods described herein. Preferably, the method of the invention is performed with a minimal amount of elution buffer, to ensure that the concentration of isolated analyte in the elution buffer is maximized. More preferably, the concentration of at least one isolated analyte will be higher in the elution buffer than previously in the test sample.

After isolating the captured analytes, the analytes may be further processed by concentration or fractionation based on some chemical or physical property such as molecular weight, isoelectric point or affinity to a chemical or biochemical ligand. Fractionation methods for nucleic acids, proteins, lipids and polysaccharides are well-known in the art and are discussed in, for example, Scopes, *Protein Purification: Principles and Practice* (1982); Sambrook et al., *Molecular Cloning—A Laboratory Manual* (2nd ed.) Vol. 1-3, Cold Spring Harbor Laboratory, Cold Spring Harbor Press, N.Y., (Sambrook) (1989); and Current Protocols in Molecular Biology, F. M. Ausubel et al., eds., *Current Protocols*, a joint venture between Greene Publishing Associates, Inc. and John Wiley & Sons, Inc., (1994 Supplement) (Ausubel).

E. Detecting Isolated Analytes

After analytes have been eluted and isolated free of binding moieties, the analyte may be detected, quantified or otherwise characterized using any technique available to those of ordinary skill in the art. A feature of applying the analysis techniques of the present invention to complex test samples, is the dynamic reduction of variance in analyte concentrations for isolated analytes relative to the large range in analyte concentration found in the original test sample. This reduction in analyte concentration range allows a much larger percentage of analytes found in the original test sample to be detected and characterized without recalibrating the detection device than would be available for analyte detection using the original test sample itself. The actual reduction in analyte concentration range achieved is dependent on a variety of factors including the nature of the original test sample, and the nature and diversity of the binding moieties used. Generally, the reduction in analyte concentration variance using the techniques described herein is sufficient to allow at least 25% more preferably at least 30%, 40%, 50%, 60%, 70%, 75% or 80% of the analytes isolated to be detected without instrument re-calibration. Ideally, the present invention allows at least 90%, 95%, 98% or more of the analytes isolated to be detected without instrument re-calibration.

Detecting analytes isolated using the techniques described herein may be accomplished using any suitable method known to one of ordinary skill in the art. For example, colorimetric assays using dyes are widely available. Alternatively, detection may be accomplished spectroscopically. Spectroscopic detectors rely on a change in refractive index; ultraviolet and/or visible light absorption, or fluorescence after excitation with a suitable wavelength to detect reaction components. Exemplary detection methods include fluorimetry, absorbance, reflectance, and transmittance spectroscopy. Changes in birefringence, refractive index, or diffraction may also be used to monitor complex formation or reaction progression. Particularly useful techniques for detecting molecular interactions include surface plasmon resonance, ellipsometry, resonant mirror techniques, grating-coupled waveguide techniques, and multi-polar resonance spectroscopy. These techniques and others are well known and can readily be applied to the present invention by one skilled in the art, without undue experimentation. Many of these methods and others may be found for example, in "Spectrochemical Analysis" Ingle, J. D. and Crouch, S. R., Prentice Hall Publ. (1988) and "Analytical Chemistry" Vol. 72, No. 17.

A preferred method of detection is by mass spectroscopy. Mass spectroscopy techniques include, but are not limited to ionization (I) techniques such as matrix assisted laser desorption (MALDI), continuous or pulsed electrospray (ESI) and related methods (e.g., IONSPRAY or THERMOSPRAY), or massive cluster impact (MCI); these ion sources can be matched with detection formats including linear or non-linear reflection time-of-flight (TOF), single or multiple quadropole, single or multiple magnetic sector, Fourier Transform ion cyclotron resonance (FTICR), ion trap, and combinations thereof (e.g., ion-trap/time-of-flight). For ionization, numerous matrix/wavelength combinations (MALDI) or solvent combinations (ESI) can be employed. Subattomole levels of analyte have been detected, for example, using ESI (Valaskovic, G. A. et al., (1996) Science 273:1199-1202) or MALDI (Li, L. et al., (1996) J. Am. Chem. Soc. 118:1662-1663) mass spectrometry. ES mass spectrometry has been introduced by Fenn et al. (J. Phys. Chem. 88, 4451-59 (1984); PCT Application No. WO 90/14148) and current applications are summarized in recent review articles (R. D. Smith et al., Anal. Chem. 62, 882-89 (1990) and B. Ardrey, Electrospray Mass Spectrometry, Spectroscopy Europe, 4, 10-18 (1992)). MALDI-TOF mass spectrometry has been introduced by Hillenkamp et al. ("Matrix Assisted UV-Laser Desorption/Ionization: A New Approach to Mass Spectrometry of Large Biomolecules," Biological Mass Spectrometry (Burlingame and McCloskey, editors), Elsevier Science Publishers, Amsterdam, pp. 49-60, 1990). With ESI, the determination of molecular weights in femtomole amounts of sample is very accurate due to the presence of multiple ion peaks that may be used for the mass calculation. A preferred analysis method of the present invention utilizes Surfaces Enhanced for Laser Desorption/Ionization (SELDI), as discussed for example in U.S. Pat. No. 6,020,208. Mass spectroscopy is a particularly preferred method of detection in those embodiments of the invention where elution of analytes directly onto a mass spectrometer probe or biochip occurs, or where the elution buffer contains a matrix material or is combined with a matrix material after elution of analytes from the binding moieties.

Another method of detection widely used is electrophoresis separation based on one or more physical properties of the analyte(s) of interest. A particularly preferred embodiment for analysis of polypeptide and protein analytes is two-dimensional electrophoresis. A preferred application separates the analyte by isoelectric point in the first dimension, and by size in the second dimension. Methods for electrophoretic analysis of analytes vary widely with the analyte being studied, but techniques for identifying a particular electrophoretic method suitable for a given analyte are well known to those of skill in the art.

II. Identification of Biomarkers

Another embodiment of the present invention is the use of the beaded binding moiety libraries described above in the identification of biomarkers for the diagnosis of diseases, infection or pollution. Biomarkers may be identified in any of the samples noted above, but preferably are identified from samples, such as blood, urine, cerebrospinal fluid and the like, taken from living beings, most preferably human beings. There are several ways in which biomarkers may be identified.

A "biomarker" is virtually any biological compound, such as a protein and a fragment thereof, a peptide, a polypeptide, a proteoglycan, a glycoprotein, a lipoprotein, a carbohydrate, a lipid, a nucleic acid, an organic on inorganic chemical, a natural polymer, and a small molecule, that is present in the biological sample and that may be isolated from, or measured in, the biosample. Furthermore, a biomarker can be the entire intact molecule, or it can be a portion thereof that may be partially functional or recognized, for example, by an antibody or other specific binding protein. A biomarker can be an epitope-specific antibody. A biomarker is considered to be informative if a measurable aspect of the biomarker is associated with a given phenotype, such as a particular disease state in a living being, or level of pollution in a body of water. Such a measurable aspect may include, for example, the presence, absence, or concentration of the biomarker in the biological sample from the individual and/or its presence as part of a profile of biomarkers. Such a measurable aspect of a biomarker is defined herein as a "feature." A feature may also be a ratio of two or more measurable aspects of biomarkers, which biomarkers may or may not be of known identity, for example. A "biomarker profile" comprises at least two such features, where the features can correspond to the same or different classes of biomarkers such as, for example, a nucleic acid and a carbohydrate. A biomarker profile may also comprise at least three, four, five, 10, 20, 30 or more features. In one embodiment, a biomarker profile comprises hundreds, or even thousands, of features. In another embodiment, the biomarker profile comprises at least one measurable aspect of at least one internal standard.

A "phenotype" is an observable physical or biochemical characteristic of an organism, as determined by both genetic makeup and environmental influences. Alternatively, in the context of the present invention, a phenotype may also be associated with non-living aspects of nature, for example the phenotype of a body of water includes those aspects of the body of water that are detectable, either physically or chemically. For example, the phenotype of a lake includes the water temperature, acidity, mineral content, oxygen content, whether it is capable of sustaining life and if so, what types of life.

A "phenotypic change" is a detectable change in a parameter associated with a given phenotype. For instance, a phenotypic change may include an increase or decrease of a biomarker in a bodily fluid, where the change is associated with a disease state. A phenotypic change may further include a change in a detectable aspect of a given state of a patient that is not a change in a measurable aspect of a biomarker. For example, a change in phenotype may include a detectable change in body temperature, respiration rate, pulse, blood pressure, or other physiological parameter. Such changes can be determined via clinical observation and measurement using conventional techniques that are well-known to the skilled artisan. As used herein, "conventional techniques" are those techniques that classify an individual based on phenotypic changes without obtaining a biomarker profile according to the present invention.

Using the claimed invention to identifying diagnostic biomarkers in a species or tissue requires the availability of at least two biosamples. The biosamples provided may be from a control group and a test group, a control group and a test individual, taken from the same individual at different times or any other permutation that is readily apparent to one of skill in the art.

Each biosample obtained is treated with a beaded binding moiety library as described herein. In this way, more putative biomarkers are available for analysis, as described in the examples section herein below. This occurs because the binding moiety library narrows the variance in the concentration range of analytes present in the sample, thereby allowing both low abundance and high abundance analytes to be detected.

After treatment with a binding moiety library of the present invention, analytes for each of the biosamples that are bound by the binding moieties are eluted and pooled separately. The pooled samples are then analyzed to determine if any of the common analytes in the samples display differential expression (enhanced expression in one biosample vs. the other), or is expressed in one biosample but not the other. Analytes displaying such differential expression are considered putative biomarkers for the phenotypic change or difference observed between the sources of the respective biosamples. Further statistical and analytic testing may then be performed to correlate the biomarker with the phenotypic change with a desired degree of certainty.

Preferred methods of analytical analysis for use in identifying biomarkers are that same as those described above for identifying analytes binding the binding moieties of the invention generally.

III. Kits

The present invention also includes kits containing components that allow one of ordinary skill in the art to perform the techniques described herein. The most basic of kits for this purpose provide a plurality of binding moieties, each binding moiety in an amount selected to capture a pre-determined amount of a different analyte. In some kit embodiments of the invention the binding moieties are supplied coupled to a solid support, preferably insoluble beads. In other embodiments the solid support and binding moieties are supplied separately. When supplied separately, the binding moieties and/or solid supports include a capture moiety that allows the operator of the invention to couple binding moiety to solid support during the course of practicing the invention described herein. Kits providing separate binding moieties and solid supports may optionally provide additional reagents necessary to perform the reaction coupling the binding moieties to the solid supports.

Kits of the present invention also include a plurality of containers retaining components for sample preparation and analyte isolation. Exemplary components of this nature include one or more wash solutions sufficient for removing unbound material from a binding moiety specifically bound to an analyte, and at least one elution solution sufficient to release analyte specifically bound by a binding moiety.

Kit embodiments may optionally include instructions for using the library of binding moieties in the methods of this invention.

Although the forgoing invention has been described in some detail by way of illustration and example for clarity and understanding, it will be readily apparent to one ordinary skill in the art in light of the teachings of this invention that certain variations, changes, modifications and substitution of equivalents may be made thereto without necessarily departing from the spirit and scope of this invention. As a result, the embodiments described herein are subject to various modifications, changes and the like, with the scope of this invention being determined solely by reference to the claims appended hereto. Those of skill in the art will readily recognize a variety of non-critical parameters that could be changed, altered or modified to yield essentially similar results.

While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention.

As can be appreciated from the disclosure above, the present invention has a wide variety of applications. The invention is further illustrated by the following examples, which are only illustrative and are not intended to limit the definition and scope of the invention in any way.

EXAMPLES

Example 1

Reduction of Range of Concentrations of Human Serum Proteins

This example illustrates how one embodiment of the invention described above may be applied to a complex biological sample, in this case human serum. In this example, a reduction in the variance of serum protein concentrations is achieved by selectively adsorbing serum proteins to hexapeptides coupled to insoluble beads. More than $1 \times 10^6$ possible permutations of hexapeptide are represented in the binding moiety population of the example, in the form of a combinatorial library of split, recombine and pool beads. In this format, high abundance serum analytes, such as albumin, are bound to a hexapeptide binding moiety, but only to a level equal to saturation of the particular binding moiety. In contrast, low abundance serum analytes are bound almost in their entirety, as the amount of binding moiety recognizing the low abundance analyte is not limiting. The result of this selective binding is a reduction in the range of analyte concentrations for proteins recognized by the binding moieties of used, without the risk of losing low abundance analytes inherent in methods that seek to selectively remove high abundance analytes. Consequently, a large percentage of the serum analytes isolated using the method can be detected in one batch analysis without a recalibration of the detection device. This contrasts with the situation presented when detecting the same analytes in a serum test sample where the detection device would have to be recalibrated repeatedly in order to detect the same analytes in untreated sera. In this example, 30 mL serum was centrifuged at 4° C., 14,000 rpm for 15 minutes and all lipid material carefully removed from the top layer. The remaining serum was filtered through a 0.8 μm filter, and then through 0.45 um filter. 500 μl of this filtered serum was set aside as a non-equalized control sample. Approximately 1 mL of hexapeptide library (swollen in 20% methanol overnight, then 20 mM sodium citrate buffer containing 140 mM sodium chloride pH 7 overnight, and washed 3 times to remove fine particle material) was aliquoted into each of three gravity flow columns. Each aliquot of hexapeptide library was incubated with a 7.6 mL aliquot of filtered serum for 2 hours at room temperature with gentle agitation. After incubation, the columns were allowed to drain and the volume collected represented the flow-through. 1 mL of the flow-through was saved for analysis. The columns were then immediately washed with 20 mL citrate buffer (20 mM sodium citrate, 140 mM sodium chloride, pH=7). The first 1 mL of the wash was additionally collected for analysis. After washing, several 200 uL aliquots of resin from each of the three column replicates were removed and processed as next described. To one 200 μl aliquot of resin from each replicate, the sample was heated with 200 uL 2×LDS buffer+DTT reducing agent (prepared by mixing 500 uL 4×LDS, 200 uL 10×DTT, and 300 uL dH2O) for 10 minutes at 90° C. After the samples were cooled, they were centrifuged at 2,000 rpm for 1 minute. The supernatant was collected and saved at −20° C. for 1D-gel analysis. To a second 200 uL aliquot of resin from each replicate, the sample was incubated with 400 uL 6M urea, for 1 hour in batch format, with gentle agitation. The sample was then centrifuged at 2,000 rpm for 1 minute to pellet the hexamer ligand bead library and the supernatant was collected for analysis by SELDI-mass spectrometry. To a third 200 uL aliquot of resin from each replicate, the sample was incubated with 400 uL of 6MGuHCl for 1 hour in batch format, with gentle agitation. The sample was then centrifuged at 2,000 rpm for 1 minute to pellet the hexamers ligand bead library and the supernatant was collected for analysis by SELDI-mass spectrometry.

All samples retained for SELDI-mass spectrometry analysis were subsequently processed on IMAC-Cu ProteinChip Arrays. IMAC arrays were first prepared by incubating 5 min with 50 uL of 100 mM CuSO4 to charge the surface with Cu. Incubation was done at room temperature with constant shaking. After the incubation period, excess CuSO4 was removed by rinsing the arrays with distilled water. The charged IMAC-Cu arrays were then neutralized with 100 mM Na acetate pH 4.0 for 5 min at room temperature with constant shaking. After the incubation time, the Na acetate was removed and the IMAC-Cu arrays were rinsed with distilled water. IMAC-Cu arrays were next pre-conditioned twice with 150 ul binding buffer (0.1 M NaPO$_4$, 0.5 M NaCl, pH 7) for 5 min with constant shaking at room temperature. After preconditioning, this buffer was removed and a fresh 90 ul aliquot of binding buffer was added, followed by and additional 10 ul of sample from the equalization experiment (total incubation volume of 100 ul). The samples were then incubated on the IMAC-Cu arrays for 30 min with constant shaking. After incubation, the excess sample volume was removed and the arrays washed three times with 150 uL of binding buffer; 5 min each wash with constant shaking. After the final wash, the IMAC-Cu arrays were rinsed twice with 150 uL distilled water, then dried. As a final step, 1 uL of 50% saturated SPA (in 50% acetonitrile, 0.5% trifluoroacetic acid) was added to each spot, dried, then the matrix addition repeated with an additional 1 ul 50% SPA. The arrays were then ready to be analyzed by SELDI-mass spectrometry.

Figure 6:
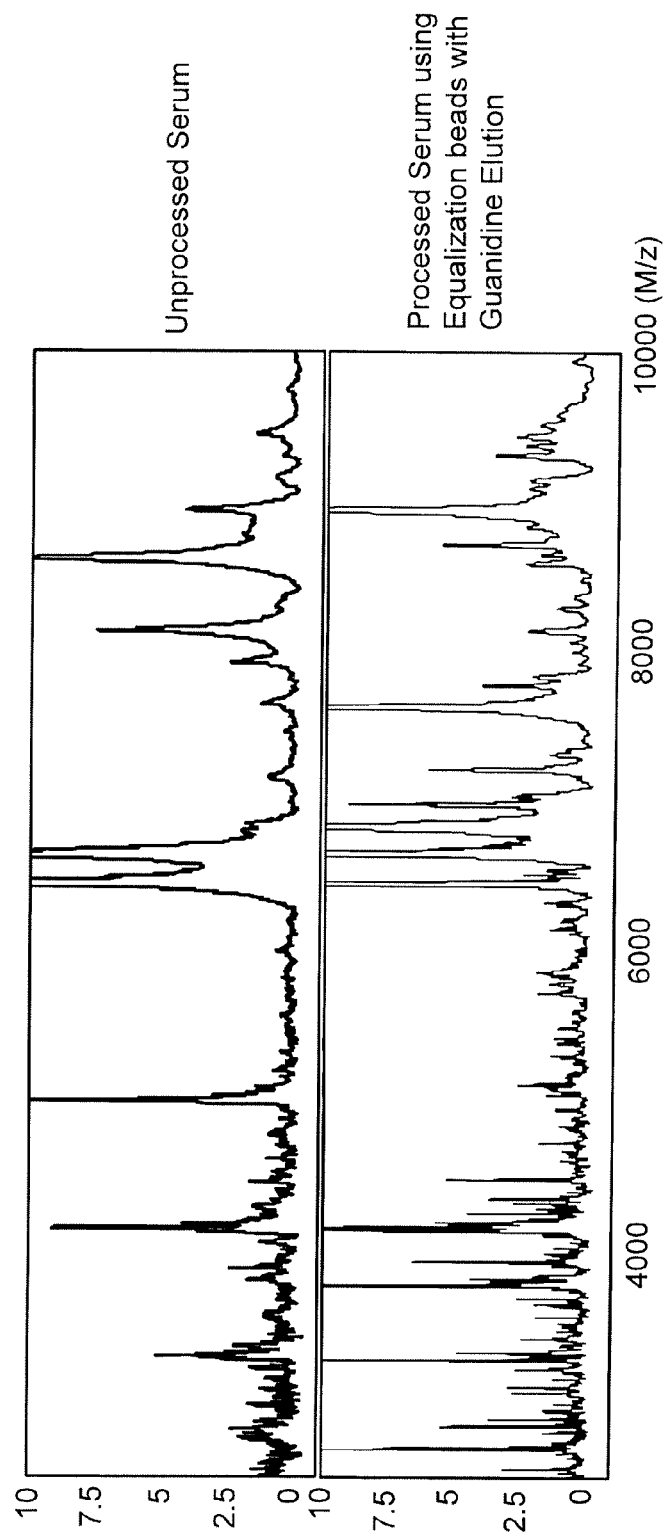
FIG. 6 is a mass spectrometry comparison of sample before and after processing with the Equalization beads. Mass range 2.5 kDa to 10 kDa. The experiment was conducted according to Example 1.
Figure 7:
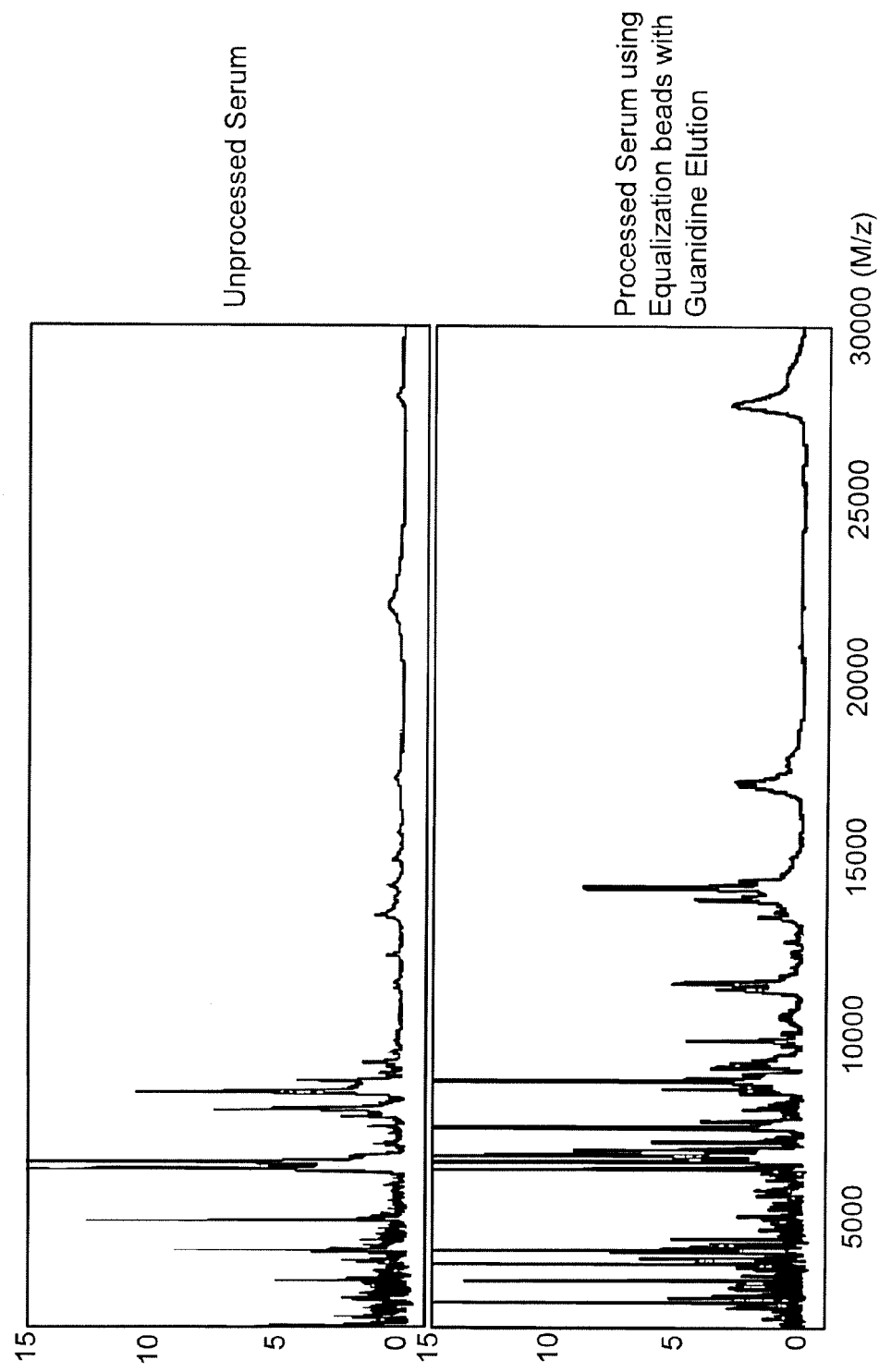
FIG. 7 is a comparison of sample before and after processing with the Equalization beads. Mass range 2 kDa to 30 kDa. The experiment was conducted according to Example 1.
Figure 8:
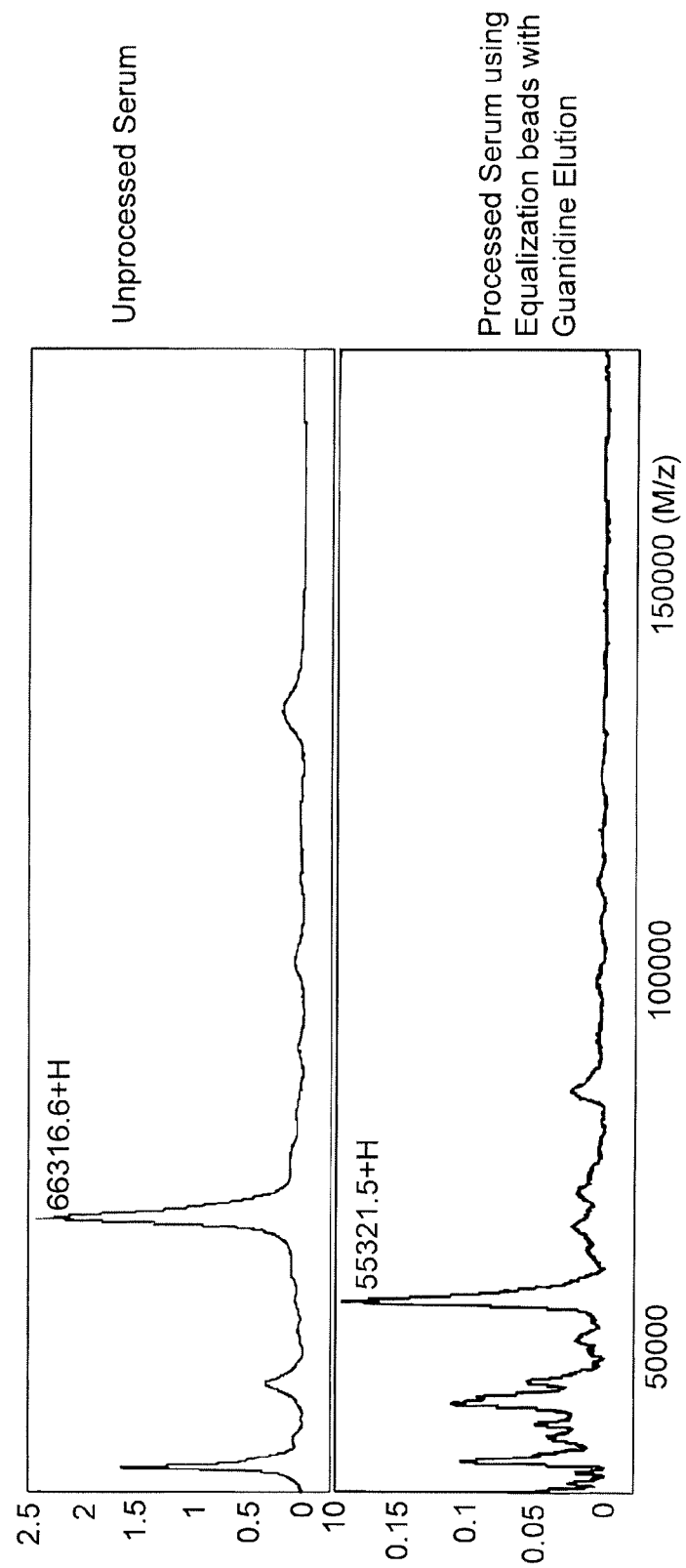
FIG. 8 is a comparison of sample before and after processing with the Equalization beads. Mass range 30 kDa to 180 kDa. The experiment was conducted according to Example 1.
Figure 9:
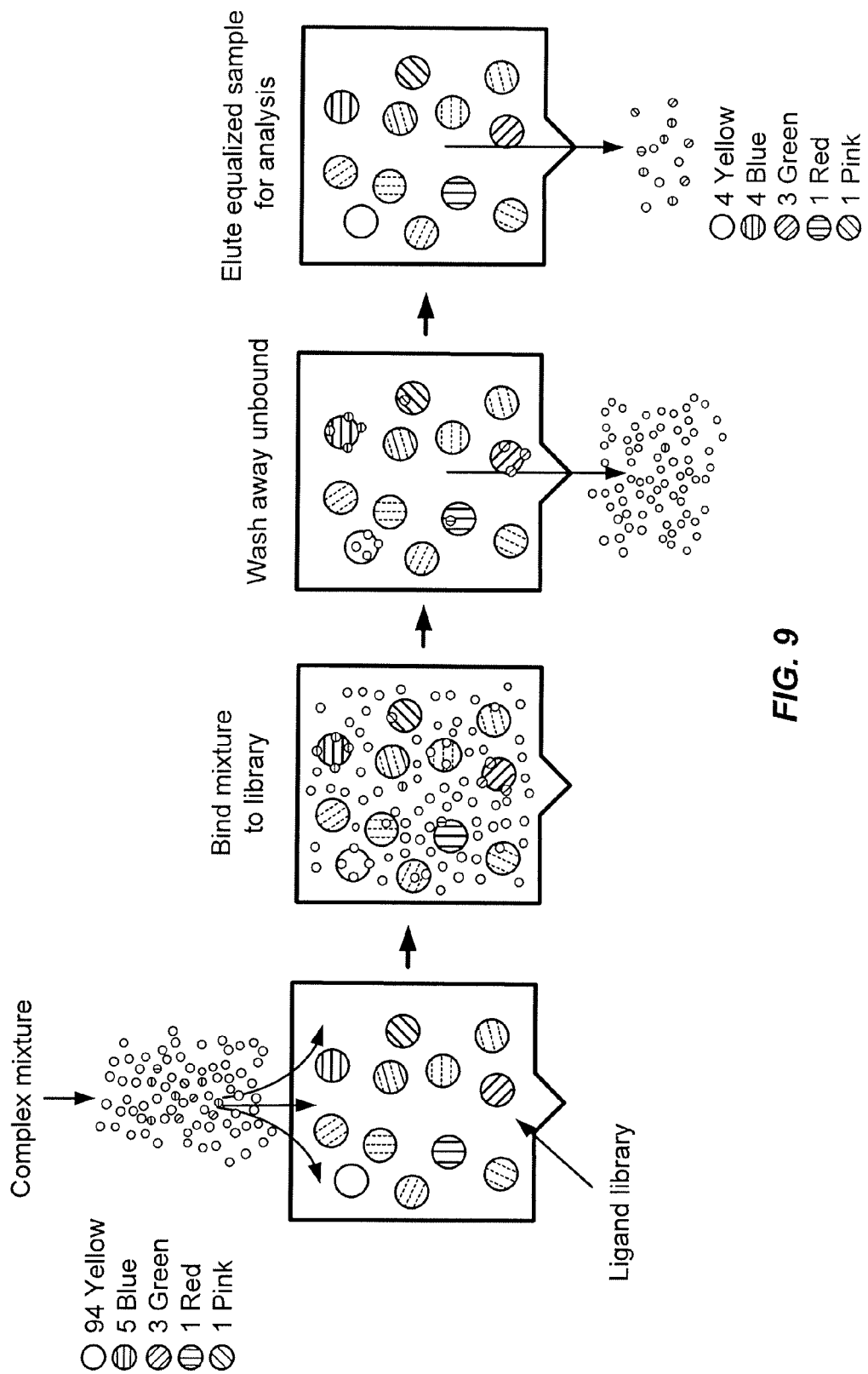
FIG. 9 is a graphical depiction of one embodiment of the equalizer bead concept of the present invention.

A SELDI-mass spectrometry comparison of filtered serum before and after equalization is depicted in FIGS. 6-8. Analysis of the sample by mass spectrometry showed increased evenness in the peak heights and an increase in the number of peaks seen, as the decrease in abundant molecules also decreased the ion suppression that hid peaks in the native sample. This methodology is anticipated to increase the number of detectable analytes in a complex solution, such as blood serum, by at least 0.5, more likely 1, 2, 3 or more orders of magnitude over the number of detectable analytes using the original complex solution not subjected to the methodology of the invention.

It has been found that libraries of hexapeptides having as few as 700,000 different members produce similar results on serum as a library of 64 million members or 3 million members.

TABLE 1

Peak detection of proteins with S/N ratio >3 from Serum not processed with Equalization Beads. Total Peaks detected = 191

| M/z | Mass | TOF | Intensity | MZ Area | TOF Area | S/N |
|---|---|---|---|---|---|---|
| 2015.66 | 2014.65 | 17.177 | 6.4172 | 127.90 | 0.5429 | 49.02 |
| 2036.48 | 2035.47 | 17.265 | 5.3084 | 143.63 | 0.6038 | 40.64 |
| 2088.13 | 2087.12 | 17.482 | 2.2443 | 48.87 | 0.2033 | 17.28 |
| 2158.14 | 2157.14 | 17.771 | 1.1293 | 8.45 | 0.0346 | 8.76 |
| 2236.71 | 2235.71 | 18.090 | 1.4596 | 19.01 | 0.0765 | 11.41 |
| 2274.25 | 2273.24 | 18.240 | 2.6476 | 59.30 | 0.2367 | 20.78 |
| 2297.37 | 2296.36 | 18.332 | 1.7593 | 25.74 | 0.1021 | 13.84 |
| 2348.05 | 2347.05 | 18.532 | 1.1940 | 16.12 | 0.0632 | 9.44 |
| 2387.06 | 2386.06 | 18.685 | 1.0549 | 10.47 | 0.0408 | 8.38 |
| 2433.77 | 2432.76 | 18.865 | 1.1221 | 9.13 | 0.0352 | 8.95 |
| 2510.49 | 2509.48 | 19.159 | 1.1701 | 13.08 | 0.0497 | 9.41 |
| 2548.37 | 2547.36 | 19.302 | 1.4879 | 17.14 | 0.0645 | 12.01 |
| 2588.13 | 2587.13 | 19.451 | 1.1253 | 24.23 | 0.0903 | 9.12 |
| 2645.66 | 2644.65 | 19.665 | 0.8016 | 6.61 | 0.0244 | 6.53 |
| 2672.54 | 2671.53 | 19.764 | 0.7100 | 7.81 | 0.0287 | 5.80 |
| 2701.93 | 2700.92 | 19.872 | 0.6059 | 1.89 | 0.0069 | 4.96 |
| 2714.04 | 2713.03 | 19.916 | 0.7967 | 5.25 | 0.0192 | 6.53 |
| 2744.23 | 2743.22 | 20.026 | 1.5753 | 15.67 | 0.0569 | 12.96 |
| 2765.83 | 2764.82 | 20.105 | 1.9933 | 35.32 | 0.1277 | 16.43 |
| 2798.60 | 2797.60 | 20.223 | 1.8114 | 17.06 | 0.0614 | 14.98 |
| 2822.57 | 2821.56 | 20.309 | 2.2505 | 28.31 | 0.1013 | 18.66 |
| 2841.99 | 2840.98 | 20.378 | 1.0515 | 13.66 | 0.0487 | 8.73 |
| 2874.68 | 2873.68 | 20.494 | 1.3501 | 16.29 | 0.0578 | 11.25 |
| 2882.13 | 2881.12 | 20.521 | 1.0852 | 7.18 | 0.0254 | 9.05 |
| 2986.19 | 2985.19 | 20.886 | 1.6218 | 16.72 | 0.0582 | 13.66 |
| 3008.50 | 3007.50 | 20.964 | 0.7147 | 2.51 | 0.0087 | 6.03 |
| 3035.73 | 3034.72 | 21.058 | 0.6588 | 4.37 | 0.0151 | 5.58 |
| 3051.05 | 3050.04 | 21.111 | 0.3948 | 1.66 | 0.0057 | 3.35 |
| 3069.95 | 3068.95 | 21.176 | 0.4739 | 1.33 | 0.0046 | 4.02 |
| 3092.47 | 3091.47 | 21.253 | 1.1918 | 16.40 | 0.0561 | 10.14 |
| 3114.57 | 3113.56 | 21.328 | 0.4997 | 1.64 | 0.0056 | 4.26 |
| 3151.05 | 3150.05 | 21.452 | 0.6513 | 5.28 | 0.0179 | 5.57 |
| 3164.53 | 3163.52 | 21.498 | 0.9793 | 11.19 | 0.0378 | 8.39 |
| 3232.23 | 3231.22 | 21.725 | 1.5813 | 18.92 | 0.0633 | 13.63 |
| 3243.48 | 3242.47 | 21.763 | 0.7721 | 6.38 | 0.0213 | 6.66 |
| 3298.21 | 3297.21 | 21.945 | 3.4654 | 36.61 | 0.1212 | 30.07 |
| 3313.89 | 3312.88 | 21.997 | 5.1135 | 76.84 | 0.2537 | 44.43 |
| 3333.83 | 3332.82 | 22.063 | 2.5432 | 37.75 | 0.1242 | 22.14 |
| 3384.92 | 3383.91 | 22.230 | 2.1432 | 65.06 | 0.2129 | 18.75 |
| 3407.63 | 3406.63 | 22.304 | 1.0824 | 12.54 | 0.0408 | 9.49 |
| 3429.51 | 3428.51 | 22.375 | 0.6049 | 3.05 | 0.0099 | 5.31 |
| 3452.91 | 3451.90 | 22.451 | 0.8204 | 7.29 | 0.0236 | 7.22 |
| 3476.39 | 3475.38 | 22.527 | 0.5334 | 4.42 | 0.0142 | 4.71 |
| 3503.26 | 3502.25 | 22.614 | 0.5524 | 2.93 | 0.0094 | 4.89 |
| 3511.64 | 3510.63 | 22.641 | 0.4732 | 2.83 | 0.0091 | 4.19 |
| 3528.97 | 3527.96 | 22.696 | 0.4620 | 5.10 | 0.0163 | 4.10 |
| 3546.06 | 3545.06 | 22.751 | 0.5973 | 6.70 | 0.0214 | 5.30 |
| 3568.26 | 3567.25 | 22.821 | 1.0034 | 9.59 | 0.0305 | 8.93 |

TABLE 1-continued

Peak detection of proteins with S/N ratio >3 from Serum not processed with Equalization Beads. Total Peaks detected = 191

| M/z | Mass | TOF | Intensity | MZ Area | TOF Area | S/N |
|---|---|---|---|---|---|---|
| 3590.14 | 3589.14 | 22.891 | 1.0356 | 32.09 | 0.1018 | 9.23 |
| 3623.82 | 3622.81 | 22.998 | 0.4337 | 3.89 | 0.0123 | 3.88 |
| 3637.24 | 3636.23 | 23.040 | 0.4513 | 6.62 | 0.0208 | 4.04 |
| 3694.92 | 3693.91 | 23.221 | 0.5609 | 5.95 | 0.0186 | 5.05 |
| 3729.43 | 3728.42 | 23.329 | 0.4638 | 2.79 | 0.0087 | 4.19 |
| 3764.53 | 3763.52 | 23.438 | 0.4174 | 1.51 | 0.0047 | 3.78 |
| 3805.09 | 3804.09 | 23.563 | 0.8459 | 10.90 | 0.0336 | 7.69 |
| 3823.32 | 3822.31 | 23.619 | 1.7052 | 28.82 | 0.0886 | 15.54 |
| 3848.08 | 3847.07 | 23.695 | 1.0869 | 14.13 | 0.0433 | 9.93 |
| 3855.69 | 3854.69 | 23.719 | 0.8424 | 8.51 | 0.0260 | 7.70 |
| 3898.88 | 3897.87 | 23.850 | 2.3732 | 28.05 | 0.0854 | 21.77 |
| 3921.25 | 3920.25 | 23.919 | 1.1576 | 12.73 | 0.0387 | 10.64 |
| 3942.17 | 3941.16 | 23.982 | 0.5628 | 6.01 | 0.0182 | 5.18 |
| 3966.53 | 3965.52 | 24.056 | 0.5595 | 7.51 | 0.0227 | 5.16 |
| 3980.76 | 3979.76 | 24.099 | 0.4952 | 3.90 | 0.0118 | 4.58 |
| 4027.93 | 4026.93 | 24.240 | 0.3813 | 2.66 | 0.0080 | 3.54 |
| 4058.52 | 4057.52 | 24.332 | 0.5159 | 5.65 | 0.0169 | 4.80 |
| 4076.90 | 4075.89 | 24.386 | 1.2618 | 21.95 | 0.0653 | 11.77 |
| 4161.26 | 4160.25 | 24.636 | 9.0816 | 189.47 | 0.5588 | 85.34 |
| 4187.94 | 4186.94 | 24.715 | 3.9580 | 98.13 | 0.2882 | 37.28 |
| 4211.39 | 4210.38 | 24.784 | 1.9753 | 20.07 | 0.0588 | 18.65 |
| 4225.32 | 4224.31 | 24.824 | 1.7662 | 17.90 | 0.0524 | 16.69 |
| 4237.59 | 4236.58 | 24.860 | 1.0754 | 10.50 | 0.0307 | 10.18 |
| 4259.14 | 4258.13 | 24.923 | 1.1283 | 15.93 | 0.0464 | 10.70 |
| 4277.21 | 4276.20 | 24.976 | 0.9969 | 9.99 | 0.0290 | 9.47 |
| 4306.31 | 4305.31 | 25.060 | 1.4922 | 28.79 | 0.0835 | 14.21 |
| 4317.27 | 4316.27 | 25.092 | 1.4477 | 27.75 | 0.0803 | 13.80 |
| 4387.42 | 4386.41 | 25.294 | 0.5169 | 3.99 | 0.0114 | 4.96 |
| 4421.28 | 4420.27 | 25.391 | 0.6385 | 10.89 | 0.0311 | 6.14 |
| 4476.55 | 4475.55 | 25.549 | 1.6525 | 25.13 | 0.0714 | 15.98 |
| 4498.63 | 4497.62 | 25.611 | 0.8303 | 12.41 | 0.0352 | 8.04 |
| 4524.12 | 4523.11 | 25.683 | 0.5423 | 5.72 | 0.0162 | 5.27 |
| 4545.86 | 4544.85 | 25.745 | 0.7655 | 15.04 | 0.0424 | 7.45 |
| 4574.44 | 4573.43 | 25.825 | 0.2026 | 0.70 | 0.0020 | 1.98 |
| 4589.43 | 4588.42 | 25.867 | 0.2134 | 1.61 | 0.0045 | 2.08 |
| 4610.07 | 4609.07 | 25.925 | 0.1564 | 0.29 | 0.0008 | 1.53 |
| 4632.98 | 4631.97 | 25.989 | 0.9352 | 10.71 | 0.0299 | 9.17 |
| 4653.41 | 4652.40 | 26.046 | 0.3656 | 2.90 | 0.0081 | 3.59 |
| 4673.98 | 4672.97 | 26.104 | 0.2227 | 0.95 | 0.0026 | 2.19 |
| 4705.09 | 4704.08 | 26.190 | 0.1266 | 0.60 | 0.0017 | 1.25 |
| 4721.34 | 4720.33 | 26.235 | 0.5855 | 7.57 | 0.0209 | 5.79 |
| 4746.55 | 4745.55 | 26.305 | 0.5041 | 8.28 | 0.0228 | 4.99 |
| 4760.71 | 4759.70 | 26.344 | 0.4023 | 4.44 | 0.0122 | 3.99 |
| 4776.82 | 4775.81 | 26.388 | 0.5845 | 8.39 | 0.0231 | 5.81 |
| 4795.96 | 4794.95 | 26.441 | 0.8917 | 14.07 | 0.0386 | 8.87 |
| 4817.65 | 4816.64 | 26.500 | 0.7853 | 15.13 | 0.0414 | 7.83 |
| 4900.93 | 4899.92 | 26.727 | 0.5187 | 5.56 | 0.0151 | 5.21 |
| 4946.35 | 4945.35 | 26.850 | 0.3060 | 3.20 | 0.0086 | 3.09 |
| 4963.56 | 4962.55 | 26.897 | 0.4123 | 6.74 | 0.0182 | 4.16 |
| 5010.78 | 5009.78 | 27.024 | 12.5885 | 211.54 | 0.5681 | 127.69 |
| 5031.99 | 5030.99 | 27.081 | 5.8531 | 84.84 | 0.2273 | 59.48 |
| 5053.19 | 5052.18 | 27.137 | 3.0847 | 47.31 | 0.1265 | 31.41 |
| 5074.18 | 5073.17 | 27.193 | 1.7893 | 33.97 | 0.0906 | 18.25 |
| 5109.70 | 5108.69 | 27.288 | 1.4186 | 37.78 | 0.1004 | 14.52 |
| 5174.52 | 5173.52 | 27.460 | 0.4570 | 6.47 | 0.0171 | 4.70 |
| 5215.36 | 5214.36 | 27.568 | 0.7393 | 7.91 | 0.0208 | 7.64 |
| 5234.38 | 5233.38 | 27.618 | 0.5442 | 9.17 | 0.0241 | 5.63 |
| 5273.44 | 5272.43 | 27.720 | 0.2111 | 1.10 | 0.0029 | 2.19 |
| 5340.59 | 5339.58 | 27.895 | 0.5133 | 5.40 | 0.0140 | 5.36 |
| 5504.23 | 5503.22 | 28.318 | 0.3130 | 3.85 | 0.0099 | 3.32 |
| 5525.79 | 5524.79 | 28.373 | 0.3048 | 4.10 | 0.0105 | 3.24 |
| 5584.59 | 5583.58 | 28.523 | 0.4938 | 16.84 | 0.0429 | 5.27 |
| 5710.82 | 5709.81 | 28.842 | 0.2989 | 6.40 | 0.0161 | 3.23 |
| 5758.22 | 5757.21 | 28.961 | 0.3075 | 2.85 | 0.0071 | 3.33 |
| 5832.21 | 5831.20 | 29.146 | 0.4003 | 4.57 | 0.0114 | 4.37 |
| 5871.67 | 5870.66 | 29.244 | 0.3528 | 4.17 | 0.0103 | 3.86 |
| 5885.14 | 5884.13 | 29.277 | 0.3028 | 7.90 | 0.0195 | 3.32 |
| 6013.84 | 6012.83 | 29.595 | 0.7071 | 19.42 | 0.0477 | 7.84 |
| 6034.06 | 6033.06 | 29.644 | 0.4344 | 5.55 | 0.0136 | 4.83 |
| 6396.04 | 6395.03 | 30.517 | 3.0543 | 118.14 | 0.2814 | 35.06 |
| 6455.26 | 6454.25 | 30.657 | 26.1287 | 771.78 | 1.8272 | 301.52 |
| 6477.39 | 6476.38 | 30.710 | 12.0491 | 218.47 | 0.5159 | 139.32 |
| 6499.00 | 6497.99 | 30.761 | 7.2773 | 135.33 | 0.3190 | 84.31 |
| 6521.19 | 6520.18 | 30.813 | 5.3012 | 97.81 | 0.2302 | 61.54 |

TABLE 1-continued

Peak detection of proteins with S/N ratio >3 from Serum not processed with Equalization Beads. Total Peaks detected = 191

| M/z | Mass | TOF | Intensity | MZ Area | TOF Area | S/N |
|---|---|---|---|---|---|---|
| 6542.80 | 6541.79 | 30.864 | 4.2675 | 88.66 | 0.2083 | 49.63 |
| 6638.04 | 6637.03 | 31.087 | 20.2348 | 631.52 | 1.4750 | 237.36 |
| 6654.30 | 6653.29 | 31.125 | 19.0952 | 360.62 | 0.8401 | 224.32 |
| 6675.85 | 6674.84 | 31.175 | 9.8609 | 187.44 | 0.4359 | 116.07 |
| 6698.42 | 6697.41 | 31.227 | 6.2424 | 112.83 | 0.2620 | 73.63 |
| 6718.01 | 6717.00 | 31.273 | 4.2544 | 83.96 | 0.1946 | 50.27 |
| 6739.45 | 6738.44 | 31.322 | 2.7267 | 46.03 | 0.1065 | 32.28 |
| 6765.34 | 6764.34 | 31.382 | 1.9976 | 39.64 | 0.0916 | 23.70 |
| 6810.67 | 6809.66 | 31.487 | 2.0664 | 79.46 | 0.1831 | 24.62 |
| 6858.73 | 6857.73 | 31.597 | 1.8896 | 104.59 | 0.2400 | 22.61 |
| 7151.49 | 7150.48 | 32.262 | 0.9514 | 22.94 | 0.0516 | 11.69 |
| 7172.92 | 7171.91 | 32.310 | 1.0333 | 43.31 | 0.0971 | 12.72 |
| 7472.88 | 7471.87 | 32.977 | 0.4560 | 13.01 | 0.0286 | 5.77 |
| 7617.94 | 7616.93 | 33.294 | 0.4693 | 11.51 | 0.0251 | 6.02 |
| 7654.14 | 7653.13 | 33.373 | 1.3314 | 67.51 | 0.1465 | 17.12 |
| 7827.96 | 7826.96 | 33.748 | 0.2802 | 7.57 | 0.0163 | 3.66 |
| 7926.90 | 7925.89 | 33.960 | 2.4904 | 114.75 | 0.2450 | 32.85 |
| 7958.23 | 7957.23 | 34.027 | 1.3527 | 31.25 | 0.0665 | 17.89 |
| 8133.31 | 8132.30 | 34.398 | 7.5286 | 658.02 | 1.3865 | 101.22 |
| 8303.10 | 8302.09 | 34.754 | 0.8155 | 44.66 | 0.0931 | 11.14 |
| 8365.08 | 8364.07 | 34.883 | 0.5422 | 19.48 | 0.0405 | 7.45 |
| 8612.18 | 8611.18 | 35.393 | 10.6716 | 1028.00 | 2.1038 | 150.06 |
| 8774.36 | 8773.35 | 35.723 | 2.1558 | 178.91 | 0.3625 | 30.78 |
| 8940.04 | 8939.03 | 36.058 | 4.2497 | 277.17 | 0.5570 | 61.65 |
| 9028.23 | 9027.22 | 36.235 | 0.5131 | 9.18 | 0.0184 | 7.51 |
| 9116.51 | 9115.50 | 36.411 | 0.6114 | 14.83 | 0.0295 | 9.02 |
| 9162.72 | 9161.71 | 36.503 | 0.8263 | 59.88 | 0.1189 | 12.25 |
| 9307.46 | 9306.45 | 36.789 | 0.5852 | 23.46 | 0.0462 | 8.80 |
| 9454.10 | 9453.09 | 37.077 | 1.5935 | 140.29 | 0.2741 | 24.30 |
| 9585.08 | 9584.07 | 37.332 | 0.1746 | 4.40 | 0.0085 | 2.70 |
| 9683.68 | 9682.67 | 37.523 | 0.2391 | 6.15 | 0.0119 | 3.73 |
| 9743.77 | 9742.76 | 37.639 | 0.4345 | 27.31 | 0.0525 | 6.82 |
| 10072.71 | 10071.70 | 38.267 | 0.2760 | 15.39 | 0.0291 | 4.47 |
| 11533.88 | 11532.87 | 40.940 | 0.2410 | 19.15 | 0.0339 | 4.56 |
| 11691.05 | 11690.04 | 41.217 | 0.2518 | 35.15 | 0.0617 | 4.84 |
| 12454.78 | 12453.77 | 42.538 | 0.5778 | 57.72 | 0.0983 | 12.12 |
| 13574.94 | 13573.93 | 44.405 | 1.1111 | 178.32 | 0.2910 | 26.75 |
| 13715.41 | 13714.41 | 44.633 | 0.4473 | 42.34 | 0.0686 | 10.97 |
| 13866.02 | 13865.01 | 44.877 | 0.3384 | 35.35 | 0.0570 | 8.46 |
| 14034.19 | 14033.19 | 45.148 | 0.2951 | 53.00 | 0.0849 | 7.55 |
| 14392.29 | 14391.28 | 45.719 | 0.5330 | 106.02 | 0.1676 | 14.32 |
| 15118.66 | 15117.65 | 46.855 | 0.3627 | 57.41 | 0.0886 | 10.83 |
| 15313.34 | 15312.33 | 47.155 | 0.1527 | 18.28 | 0.0280 | 4.70 |
| 15870.49 | 15869.48 | 48.003 | 0.1483 | 34.49 | 0.0519 | 4.99 |
| 16659.22 | 16658.21 | 49.178 | 0.1152 | 23.78 | 0.0350 | 4.45 |
| 17261.53 | 17260.53 | 50.057 | 0.2182 | 48.44 | 0.0702 | 9.49 |
| 17403.26 | 17402.25 | 50.262 | 0.2735 | 94.70 | 0.1356 | 12.26 |
| 22185.18 | 22184.17 | 56.732 | 0.6056 | 798.59 | 1.0136 | 49.97 |
| 28054.19 | 28053.18 | 63.781 | 0.2571 | 107.68 | 0.1221 | 39.27 |
| 29051.79 | 29050.78 | 64.903 | 0.1030 | 74.85 | 0.0832 | 16.04 |
| 33245.74 | 33244.73 | 69.421 | 1.6601 | 1750.64 | 1.8258 | 281.43 |
| 34281.46 | 34280.45 | 70.492 | 0.5196 | 597.67 | 0.6025 | 89.96 |
| 39898.16 | 39897.15 | 76.038 | 0.0257 | 11.52 | 0.0110 | 4.98 |
| 44457.39 | 44456.39 | 80.258 | 0.3417 | 989.32 | 0.8917 | 69.77 |
| 49939.53 | 49938.52 | 85.055 | 0.0226 | 19.83 | 0.0169 | 4.91 |
| 51350.04 | 51349.03 | 86.246 | 0.0499 | 94.72 | 0.0792 | 10.85 |
| 55656.75 | 55655.74 | 89.784 | 0.0711 | 186.88 | 0.1514 | 15.47 |
| 59215.94 | 59214.93 | 92.607 | 0.1083 | 250.62 | 0.1967 | 23.63 |
| 66317.60 | 66316.59 | 97.995 | 2.2783 | 6680.56 | 4.9211 | 498.39 |
| 72737.16 | 72736.15 | 102.622 | 0.1259 | 350.29 | 0.2456 | 27.61 |
| 75001.97 | 75000.96 | 104.206 | 0.1127 | 216.04 | 0.1488 | 24.73 |
| 80013.65 | 80012.64 | 107.627 | 0.0678 | 279.89 | 0.1869 | 14.91 |
| 88591.36 | 88590.35 | 113.242 | 0.0472 | 171.17 | 0.1093 | 10.41 |
| 99724.32 | 99723.31 | 120.139 | 0.0857 | 436.66 | 0.2624 | 18.82 |
| 110663.70 | 110662.70 | 126.550 | 0.0315 | 123.51 | 0.0705 | 7.11 |
| 115751.09 | 115750.08 | 129.423 | 0.0392 | 84.89 | 0.0477 | 9.03 |
| 116910.94 | 116909.93 | 130.069 | 0.0411 | 256.88 | 0.1413 | 9.53 |
| 132576.48 | 132575.47 | 138.501 | 0.2015 | 1519.36 | 0.7867 | 49.62 |
| 175561.80 | 175560.79 | 159.360 | 0.0192 | 204.64 | 0.0927 | 5.21 |

TABLE 2

Peak detection of proteins with S/N ratio >3 from Serum after processing with Equalization Beads. Total Peaks detected = 271

| M/z | Mass | TOF | Intensity | MZ Area | TOF Area | S/N |
|---|---|---|---|---|---|---|
| 2021.84 | 2020.83 | 17.207 | 0.6376 | 12.12 | 0.0503 | 8.96 |
| 2067.93 | 2066.93 | 17.398 | 0.6601 | 6.51 | 0.0267 | 9.31 |
| 2087.13 | 2086.12 | 17.476 | 0.7201 | 7.41 | 0.0303 | 10.18 |
| 2106.09 | 2105.09 | 17.554 | 0.4864 | 3.56 | 0.0145 | 6.89 |
| 2180.24 | 2179.23 | 17.853 | 0.5382 | 3.23 | 0.0129 | 7.67 |
| 2221.86 | 2220.85 | 18.019 | 1.4170 | 8.54 | 0.0339 | 20.27 |
| 2240.96 | 2239.96 | 18.095 | 0.5589 | 6.06 | 0.0240 | 8.01 |
| 2266.94 | 2265.93 | 18.198 | 0.5494 | 3.98 | 0.0157 | 7.89 |
| 2293.08 | 2292.07 | 18.300 | 0.3779 | 2.12 | 0.0083 | 5.44 |
| 2339.18 | 2338.18 | 18.480 | 0.9868 | 7.77 | 0.0301 | 14.26 |
| 2378.63 | 2377.62 | 18.632 | 0.6337 | 4.75 | 0.0183 | 9.19 |
| 2396.27 | 2395.27 | 18.700 | 0.5728 | 5.76 | 0.0221 | 8.32 |
| 2439.97 | 2438.96 | 18.867 | 1.0408 | 6.19 | 0.0235 | 15.17 |
| 2467.12 | 2466.12 | 18.969 | 0.9706 | 8.52 | 0.0322 | 14.18 |
| 2497.92 | 2496.92 | 19.086 | 0.9600 | 7.48 | 0.0281 | 14.06 |
| 2526.24 | 2525.23 | 19.192 | 0.8088 | 7.31 | 0.0273 | 11.88 |
| 2553.87 | 2552.86 | 19.295 | 2.9512 | 30.44 | 0.1132 | 43.44 |
| 2625.36 | 2624.35 | 19.559 | 0.5117 | 2.40 | 0.0088 | 7.58 |
| 2655.34 | 2654.33 | 19.669 | 0.9776 | 9.38 | 0.0343 | 14.51 |
| 2683.62 | 2682.62 | 19.772 | 19.4999 | 144.76 | 0.5259 | 290.17 |
| 2706.16 | 2705.15 | 19.853 | 2.6950 | 27.91 | 0.1010 | 40.18 |
| 2729.04 | 2728.03 | 19.936 | 1.1192 | 9.74 | 0.0351 | 16.72 |
| 2801.03 | 2800.03 | 20.194 | 1.4372 | 7.80 | 0.0278 | 21.60 |
| 2841.72 | 2840.71 | 20.338 | 5.3061 | 38.45 | 0.1359 | 80.01 |
| 2864.83 | 2863.82 | 20.420 | 0.9591 | 9.76 | 0.0344 | 14.49 |
| 2889.55 | 2888.55 | 20.507 | 3.5170 | 27.58 | 0.0967 | 53.24 |
| 2930.16 | 2929.15 | 20.649 | 0.6606 | 5.11 | 0.0178 | 10.03 |
| 2946.66 | 2945.66 | 20.706 | 1.4513 | 12.23 | 0.0425 | 22.07 |
| 2991.41 | 2990.41 | 20.861 | 1.0116 | 11.76 | 0.0406 | 15.44 |
| 3068.43 | 3067.42 | 21.125 | 2.6692 | 27.74 | 0.0946 | 41.00 |
| 3091.47 | 3090.47 | 21.204 | 0.5713 | 6.74 | 0.0229 | 8.79 |
| 3104.33 | 3103.32 | 21.247 | 2.7977 | 23.84 | 0.0808 | 43.10 |
| 3128.84 | 3127.84 | 21.330 | 0.4361 | 3.91 | 0.0132 | 6.73 |
| 3159.53 | 3158.53 | 21.434 | 1.1023 | 8.52 | 0.0286 | 17.06 |
| 3186.78 | 3185.78 | 21.525 | 0.2998 | 2.51 | 0.0084 | 4.65 |
| 3203.52 | 3202.51 | 21.581 | 0.6912 | 5.44 | 0.0182 | 10.73 |
| 3224.18 | 3223.17 | 21.650 | 2.4947 | 24.72 | 0.0823 | 38.81 |
| 3237.12 | 3236.11 | 21.693 | 1.2228 | 9.75 | 0.0324 | 19.04 |
| 3247.56 | 3246.55 | 21.728 | 0.4539 | 3.69 | 0.0122 | 7.07 |
| 3289.31 | 3288.30 | 21.866 | 13.5948 | 102.60 | 0.3383 | 212.58 |
| 3311.94 | 3310.93 | 21.940 | 1.9602 | 14.93 | 0.0491 | 30.71 |
| 3336.82 | 3335.81 | 22.022 | 4.7302 | 36.91 | 0.1209 | 74.25 |
| 3346.26 | 3345.25 | 22.053 | 1.2829 | 10.27 | 0.0336 | 20.15 |
| 3358.47 | 3357.46 | 22.093 | 0.6222 | 3.29 | 0.0108 | 9.78 |
| 3373.64 | 3372.63 | 22.142 | 0.5314 | 4.59 | 0.0149 | 8.37 |
| 3385.05 | 3384.04 | 22.179 | 0.8139 | 6.98 | 0.0227 | 12.82 |
| 3415.17 | 3414.17 | 22.277 | 0.4451 | 3.75 | 0.0121 | 7.03 |
| 3427.49 | 3426.48 | 22.317 | 2.3109 | 15.05 | 0.0487 | 36.53 |
| 3438.79 | 3437.78 | 22.353 | 1.0937 | 8.77 | 0.0283 | 17.31 |
| 3447.05 | 3446.04 | 22.380 | 0.8280 | 5.94 | 0.0191 | 13.11 |
| 3459.90 | 3458.90 | 22.421 | 0.3291 | 1.87 | 0.0060 | 5.22 |
| 3467.20 | 3466.19 | 22.445 | 0.2547 | 1.29 | 0.0042 | 4.04 |
| 3485.27 | 3484.26 | 22.503 | 0.9642 | 6.74 | 0.0216 | 15.31 |
| 3495.20 | 3494.20 | 22.535 | 0.4776 | 3.13 | 0.0100 | 7.59 |
| 3506.27 | 3505.26 | 22.570 | 0.7766 | 5.56 | 0.0178 | 12.35 |
| 3524.49 | 3523.48 | 22.628 | 0.6243 | 5.34 | 0.0170 | 9.95 |
| 3530.57 | 3529.57 | 22.648 | 0.8564 | 6.82 | 0.0217 | 13.65 |
| 3552.77 | 3551.76 | 22.718 | 0.2099 | 1.07 | 0.0034 | 3.35 |
| 3573.00 | 3572.00 | 22.783 | 1.7464 | 12.44 | 0.0394 | 27.93 |
| 3642.53 | 3641.53 | 23.002 | 0.8032 | 4.85 | 0.0152 | 12.92 |
| 3660.13 | 3659.12 | 23.057 | 1.7988 | 14.34 | 0.0449 | 28.96 |
| 3683.85 | 3682.84 | 23.131 | 0.5319 | 4.38 | 0.0137 | 8.58 |
| 3702.01 | 3701.00 | 23.188 | 2.5079 | 18.21 | 0.0567 | 40.52 |
| 3746.51 | 3745.50 | 23.326 | 0.4842 | 3.69 | 0.0114 | 7.85 |
| 3774.17 | 3773.16 | 23.412 | 1.1931 | 13.41 | 0.0414 | 19.38 |
| 3789.41 | 3788.40 | 23.459 | 20.8035 | 191.08 | 0.5886 | 338.38 |
| 3811.60 | 3810.59 | 23.527 | 3.5547 | 39.12 | 0.1201 | 57.92 |
| 3833.14 | 3832.13 | 23.593 | 4.2186 | 38.90 | 0.1192 | 68.85 |
| 3848.99 | 3847.98 | 23.642 | 1.9147 | 24.85 | 0.0760 | 31.29 |
| 3887.00 | 3885.99 | 23.757 | 0.2288 | 0.81 | 0.0025 | 3.75 |
| 3907.37 | 3906.36 | 23.819 | 0.3720 | 1.41 | 0.0043 | 6.11 |
| 3916.17 | 3915.16 | 23.846 | 1.1685 | 9.34 | 0.0283 | 19.19 |
| 3931.92 | 3930.92 | 23.894 | 1.1141 | 11.11 | 0.0336 | 18.32 |
| 3946.05 | 3945.04 | 23.937 | 6.4985 | 54.40 | 0.1644 | 106.99 |

TABLE 2-continued

Peak detection of proteins with S/N ratio >3 from Serum after processing with Equalization Beads. Total Peaks detected = 271

| M/z | Mass | TOF | Intensity | MZ Area | TOF Area | S/N |
|---|---|---|---|---|---|---|
| 3960.15 | 3959.14 | 23.979 | 1.3249 | 16.05 | 0.0484 | 21.84 |
| 3979.74 | 3978.73 | 24.038 | 0.8035 | 6.65 | 0.0200 | 13.26 |
| 3996.40 | 3995.39 | 24.088 | 1.4516 | 16.40 | 0.0492 | 23.99 |
| 4013.73 | 4012.72 | 24.140 | 0.5642 | 5.43 | 0.0163 | 9.34 |
| 4037.17 | 4036.16 | 24.210 | 1.1069 | 9.51 | 0.0284 | 18.35 |
| 4079.33 | 4078.32 | 24.336 | 0.5052 | 2.25 | 0.0067 | 8.40 |
| 4101.88 | 4100.87 | 24.403 | 0.3796 | 2.87 | 0.0085 | 6.33 |
| 4116.36 | 4115.35 | 24.446 | 1.2880 | 7.31 | 0.0217 | 21.49 |
| 4123.41 | 4122.40 | 24.467 | 1.5143 | 14.62 | 0.0432 | 25.27 |
| 4147.47 | 4146.46 | 24.538 | 7.6159 | 67.57 | 0.1993 | 127.35 |
| 4161.38 | 4160.38 | 24.579 | 31.9075 | 291.83 | 0.8593 | 534.10 |
| 4181.81 | 4180.81 | 24.639 | 9.1974 | 127.91 | 0.3757 | 154.19 |
| 4205.75 | 4204.74 | 24.709 | 5.5891 | 74.72 | 0.2189 | 93.87 |
| 4227.41 | 4226.41 | 24.772 | 2.0620 | 29.87 | 0.0873 | 34.69 |
| 4249.76 | 4248.75 | 24.838 | 0.9303 | 10.38 | 0.0302 | 15.68 |
| 4272.77 | 4271.76 | 24.905 | 4.3852 | 39.31 | 0.1143 | 74.03 |
| 4295.30 | 4294.29 | 24.970 | 1.7984 | 15.14 | 0.0439 | 30.41 |
| 4316.14 | 4315.13 | 25.030 | 1.0213 | 13.60 | 0.0393 | 17.30 |
| 4334.00 | 4332.99 | 25.082 | 2.6466 | 26.85 | 0.0775 | 44.89 |
| 4356.55 | 4355.54 | 25.147 | 0.6608 | 5.66 | 0.0163 | 11.23 |
| 4367.67 | 4366.67 | 25.179 | 3.5704 | 34.89 | 0.1004 | 60.71 |
| 4386.58 | 4385.57 | 25.233 | 0.8809 | 9.31 | 0.0267 | 15.00 |
| 4412.41 | 4411.41 | 25.308 | 0.6081 | 2.58 | 0.0074 | 10.38 |
| 4435.68 | 4434.67 | 25.374 | 0.0322 | −1.50 | −0.0043 | 0.55 |
| 4445.90 | 4444.89 | 25.403 | 0.2572 | 0.77 | 0.0022 | 4.40 |
| 4494.15 | 4493.15 | 25.540 | 5.1702 | 62.47 | 0.1772 | 88.76 |
| 4516.89 | 4515.89 | 25.605 | 0.4659 | 3.11 | 0.0088 | 8.01 |
| 4540.00 | 4538.99 | 25.670 | 0.4298 | 6.56 | 0.0185 | 7.40 |
| 4573.91 | 4572.90 | 25.766 | 0.3421 | 4.53 | 0.0127 | 5.91 |
| 4607.33 | 4606.33 | 25.860 | 0.5394 | 7.83 | 0.0219 | 9.34 |
| 4622.34 | 4621.34 | 25.902 | 0.8686 | 6.78 | 0.0190 | 15.06 |
| 4651.23 | 4650.22 | 25.982 | 0.5581 | 4.93 | 0.0138 | 9.70 |
| 4680.47 | 4679.46 | 26.064 | 0.7940 | 11.05 | 0.0307 | 13.82 |
| 4717.86 | 4716.86 | 26.168 | 0.3405 | 3.24 | 0.0090 | 5.94 |
| 4737.63 | 4736.62 | 26.222 | 1.6830 | 16.14 | 0.0446 | 29.43 |
| 4746.03 | 4745.02 | 26.246 | 0.7521 | 4.57 | 0.0126 | 13.16 |
| 4759.22 | 4758.21 | 26.282 | 0.3119 | 3.05 | 0.0084 | 5.46 |
| 4787.60 | 4786.60 | 26.360 | 0.1802 | 0.99 | 0.0027 | 3.16 |
| 4816.82 | 4815.82 | 26.441 | 0.3586 | 2.73 | 0.0075 | 6.31 |
| 4829.31 | 4828.30 | 26.475 | 0.5449 | 7.60 | 0.0208 | 9.59 |
| 4849.72 | 4848.71 | 26.531 | 0.9698 | 9.32 | 0.0255 | 17.10 |
| 4869.86 | 4868.85 | 26.586 | 0.3755 | 3.13 | 0.0085 | 6.63 |
| 4899.44 | 4898.44 | 26.666 | 0.4979 | 5.97 | 0.0162 | 8.81 |
| 4918.11 | 4917.11 | 26.717 | 0.3938 | 4.58 | 0.0124 | 6.98 |
| 4963.85 | 4962.84 | 26.841 | 1.1185 | 16.74 | 0.0453 | 19.89 |
| 5062.61 | 5061.60 | 27.107 | 1.4525 | 17.55 | 0.0470 | 26.02 |
| 5094.27 | 5093.26 | 27.191 | 1.1946 | 17.48 | 0.0467 | 21.45 |
| 5108.24 | 5107.23 | 27.229 | 1.5212 | 20.68 | 0.0551 | 27.35 |
| 5128.79 | 5127.79 | 27.283 | 2.5384 | 26.47 | 0.0704 | 45.70 |
| 5145.89 | 5144.88 | 27.329 | 0.7368 | 10.95 | 0.0291 | 13.28 |
| 5173.86 | 5172.85 | 27.403 | 0.7359 | 13.56 | 0.0360 | 13.29 |
| 5187.50 | 5186.49 | 27.439 | 0.7046 | 7.49 | 0.0198 | 12.74 |
| 5205.84 | 5204.83 | 27.488 | 0.6291 | 8.47 | 0.0224 | 11.39 |
| 5274.33 | 5273.32 | 27.668 | 0.4129 | 4.92 | 0.0129 | 7.51 |
| 5315.83 | 5314.82 | 27.777 | 1.2730 | 19.00 | 0.0497 | 23.24 |
| 5341.10 | 5340.09 | 27.843 | 0.2176 | 2.07 | 0.0054 | 3.98 |
| 5359.34 | 5358.33 | 27.890 | 0.2531 | 2.97 | 0.0077 | 4.64 |
| 5402.17 | 5401.16 | 28.002 | 1.0504 | 16.14 | 0.0419 | 19.30 |
| 5433.21 | 5432.20 | 28.082 | 1.1667 | 14.37 | 0.0372 | 21.48 |
| 5454.45 | 5453.44 | 28.137 | 0.2116 | 2.89 | 0.0075 | 3.90 |
| 5504.70 | 5503.70 | 28.267 | 1.0223 | 19.86 | 0.0511 | 18.93 |
| 5546.41 | 5545.40 | 28.374 | 0.4939 | 6.77 | 0.0173 | 9.17 |
| 5609.12 | 5608.11 | 28.534 | 0.4736 | 9.68 | 0.0247 | 8.83 |
| 5624.76 | 5623.76 | 28.574 | 0.4185 | 4.48 | 0.0114 | 7.82 |
| 5682.49 | 5681.49 | 28.720 | 0.1958 | 1.06 | 0.0027 | 3.67 |
| 5733.38 | 5732.37 | 28.849 | 1.7600 | 31.18 | 0.0786 | 33.14 |
| 5755.15 | 5754.14 | 28.904 | 0.8682 | 12.82 | 0.0322 | 16.37 |
| 5797.90 | 5796.89 | 29.011 | 1.3933 | 36.06 | 0.0904 | 26.36 |
| 5847.40 | 5846.39 | 29.135 | 1.2801 | 24.84 | 0.0620 | 24.30 |
| 5874.14 | 5873.13 | 29.201 | 1.8388 | 62.45 | 0.1554 | 34.98 |
| 5934.72 | 5933.72 | 29.352 | 0.5579 | 12.73 | 0.0315 | 10.66 |
| 5978.50 | 5977.49 | 29.460 | 0.3853 | 7.29 | 0.0180 | 7.39 |
| 6013.90 | 6012.90 | 29.548 | 0.3552 | 2.90 | 0.0071 | 6.83 |
| 6032.85 | 6031.85 | 29.594 | 0.4093 | 3.60 | 0.0089 | 7.88 |
| 6133.82 | 6132.81 | 29.841 | 0.5865 | 6.96 | 0.0170 | 11.37 |
| 6162.34 | 6161.33 | 29.911 | 1.3553 | 20.48 | 0.0498 | 26.33 |
| 6184.57 | 6183.56 | 29.965 | 0.6588 | 9.78 | 0.0238 | 12.82 |
| 6216.02 | 6215.01 | 30.041 | 0.9219 | 19.68 | 0.0477 | 17.98 |
| 6236.00 | 6235.00 | 30.090 | 0.8304 | 10.75 | 0.0260 | 16.22 |
| 6255.36 | 6254.35 | 30.136 | 0.2361 | 2.34 | 0.0057 | 4.62 |
| 6320.39 | 6319.39 | 30.293 | 1.1214 | 17.58 | 0.0423 | 22.04 |
| 6342.23 | 6341.22 | 30.346 | 1.5366 | 26.64 | 0.0639 | 30.25 |
| 6456.30 | 6455.29 | 30.618 | 21.3573 | 431.55 | 1.0263 | 424.01 |
| 6498.25 | 6497.24 | 30.718 | 1.8487 | 25.84 | 0.0613 | 36.82 |
| 6521.67 | 6520.66 | 30.773 | 2.3440 | 32.22 | 0.0763 | 46.76 |
| 6551.22 | 6550.21 | 30.843 | 1.5207 | 32.41 | 0.0765 | 30.40 |
| 6614.06 | 6613.06 | 30.991 | 1.7907 | 21.31 | 0.0501 | 35.96 |
| 6653.73 | 6652.72 | 31.084 | 40.0260 | 990.54 | 2.3211 | 806.22 |
| 6696.04 | 6695.03 | 31.183 | 5.5580 | 89.50 | 0.2091 | 112.30 |
| 6718.43 | 6717.42 | 31.236 | 3.9535 | 70.52 | 0.1645 | 80.01 |
| 6740.82 | 6739.81 | 31.288 | 3.0803 | 58.81 | 0.1370 | 62.44 |
| 6763.08 | 6762.07 | 31.339 | 2.6139 | 47.31 | 0.1100 | 53.07 |
| 6832.17 | 6831.17 | 31.500 | 29.3327 | 769.05 | 1.7805 | 598.61 |
| 6852.89 | 6851.88 | 31.548 | 12.8114 | 225.11 | 0.5200 | 261.85 |
| 6873.74 | 6872.73 | 31.596 | 6.7676 | 115.78 | 0.2670 | 138.53 |
| 6895.96 | 6894.95 | 31.647 | 4.0495 | 126.91 | 0.2920 | 83.03 |
| 6968.15 | 6967.14 | 31.813 | 2.6462 | 48.81 | 0.1119 | 54.54 |
| 6987.83 | 6986.82 | 31.858 | 9.1160 | 179.49 | 0.4107 | 188.17 |
| 7007.18 | 7006.18 | 31.902 | 3.5064 | 48.01 | 0.1097 | 72.48 |
| 7035.74 | 7034.73 | 31.967 | 2.8179 | 55.45 | 0.1265 | 58.37 |
| 7054.79 | 7053.78 | 32.011 | 2.6118 | 69.35 | 0.1578 | 54.18 |
| 7219.97 | 7218.97 | 32.385 | 6.0098 | 205.68 | 0.4631 | 126.18 |
| 7323.59 | 7322.59 | 32.617 | 1.4502 | 43.84 | 0.0980 | 30.68 |
| 7354.38 | 7353.37 | 32.686 | 0.8418 | 14.96 | 0.0334 | 17.85 |
| 7426.45 | 7425.44 | 32.847 | 0.2530 | 8.63 | 0.0192 | 5.39 |
| 7632.91 | 7631.90 | 33.302 | 25.1248 | 922.09 | 2.0212 | 543.77 |
| 7697.48 | 7696.47 | 33.443 | 2.3440 | 94.17 | 0.2053 | 50.97 |
| 7781.99 | 7780.98 | 33.627 | 4.0191 | 140.62 | 0.3052 | 87.95 |
| 7839.40 | 7838.39 | 33.752 | 2.0650 | 82.17 | 0.1776 | 45.38 |
| 7929.48 | 7928.47 | 33.946 | 0.4065 | 11.97 | 0.0257 | 8.99 |
| 8003.12 | 8002.12 | 34.104 | 0.6177 | 20.19 | 0.0432 | 13.74 |
| 8070.02 | 8069.01 | 34.247 | 0.7401 | 21.61 | 0.0461 | 16.54 |
| 8141.70 | 8140.69 | 34.399 | 2.3180 | 68.48 | 0.1454 | 52.09 |
| 8158.61 | 8157.60 | 34.435 | 1.6675 | 29.11 | 0.0617 | 37.52 |
| 8251.98 | 8250.97 | 34.633 | 0.3282 | 9.23 | 0.0195 | 7.43 |
| 8294.07 | 8293.06 | 34.721 | 1.2292 | 37.02 | 0.0779 | 27.93 |
| 8372.44 | 8371.43 | 34.886 | 0.5741 | 27.10 | 0.0568 | 13.12 |
| 8484.99 | 8483.99 | 35.121 | 0.3754 | 8.50 | 0.0177 | 8.65 |
| 8589.51 | 8588.50 | 35.338 | 2.4703 | 105.46 | 0.2180 | 57.39 |
| 8651.75 | 8650.75 | 35.466 | 1.8591 | 59.08 | 0.1217 | 43.39 |
| 8713.50 | 8712.49 | 35.593 | 5.5491 | 204.46 | 0.4198 | 130.11 |
| 8756.61 | 8755.80 | 35.682 | 1.7265 | 52.13 | 0.1067 | 40.61 |
| 8833.41 | 8832.40 | 35.838 | 2.4403 | 133.47 | 0.2724 | 57.73 |
| 8939.05 | 8938.04 | 36.053 | 22.2153 | 1128.34 | 2.2880 | 529.75 |
| 9019.22 | 9018.21 | 36.216 | 2.3984 | 92.32 | 0.1862 | 57.54 |
| 9091.97 | 9090.96 | 36.362 | 2.3245 | 113.49 | 0.2282 | 56.07 |
| 9144.69 | 9143.68 | 36.468 | 2.3181 | 121.61 | 0.2437 | 56.14 |
| 9309.12 | 9308.12 | 36.796 | 3.6153 | 148.49 | 0.2952 | 88.65 |
| 9374.68 | 9373.68 | 36.926 | 2.4549 | 109.39 | 0.2167 | 60.49 |
| 9437.96 | 9436.95 | 37.051 | 2.7925 | 165.50 | 0.3267 | 69.14 |
| 9516.91 | 9515.90 | 37.207 | 1.8864 | 104.50 | 0.2055 | 46.99 |
| 9581.85 | 9580.84 | 37.334 | 1.3051 | 70.92 | 0.1390 | 32.67 |
| 9637.19 | 9636.19 | 37.443 | 1.0115 | 54.07 | 0.1056 | 25.43 |
| 9724.00 | 9722.99 | 37.612 | 0.3754 | 16.30 | 0.0317 | 9.50 |
| 9785.71 | 9784.70 | 37.732 | 0.2852 | 9.89 | 0.0192 | 7.25 |
| 9939.68 | 9938.68 | 38.029 | 0.7471 | 35.29 | 0.0679 | 19.22 |
| 10063.40 | 10062.39 | 38.267 | 4.5744 | 203.31 | 0.3889 | 118.81 |
| 10144.76 | 10143.75 | 38.422 | 0.5690 | 31.57 | 0.0601 | 14.87 |
| 10273.13 | 10272.12 | 38.666 | 0.7631 | 38.76 | 0.0734 | 20.15 |
| 10497.57 | 10496.57 | 39.089 | 0.2782 | 13.21 | 0.0247 | 7.47 |
| 10561.30 | 10560.29 | 39.208 | 0.4082 | 21.74 | 0.0406 | 11.02 |
| 10635.46 | 10634.45 | 39.346 | 0.5930 | 35.52 | 0.0661 | 16.10 |
| 10718.48 | 10717.47 | 39.500 | 0.9040 | 61.40 | 0.1139 | 24.71 |
| 10802.36 | 10801.36 | 39.656 | 0.8599 | 66.95 | 0.1236 | 23.66 |
| 10921.46 | 10920.45 | 39.875 | 0.4378 | 23.17 | 0.0426 | 12.16 |
| 11046.41 | 11045.40 | 40.104 | 0.1310 | 5.23 | 0.0096 | 3.68 |
| 11147.95 | 11146.94 | 40.289 | 0.1517 | 7.75 | 0.0141 | 4.29 |
| 11431.94 | 11430.93 | 40.802 | 1.5601 | 85.67 | 0.1542 | 45.13 |

TABLE 2-continued

Peak detection of proteins with S/N ratio >3 from Serum after processing with Equalization Beads. Total Peaks detected = 271

| M/z | Mass | TOF | Intensity | MZ Area | TOF Area | S/N |
|---|---|---|---|---|---|---|
| 11515.49 | 11514.48 | 40.952 | 3.4607 | 316.45 | 0.5666 | 100.79 |
| 11667.57 | 11666.56 | 41.223 | 5.1984 | 534.22 | 0.9496 | 153.29 |
| 11874.61 | 11873.61 | 41.590 | 0.8999 | 92.25 | 0.1626 | 26.99 |
| 12135.29 | 12134.28 | 42.047 | 0.3472 | 20.90 | 0.0365 | 10.64 |
| 12213.21 | 12212.20 | 42.183 | 0.1927 | 12.50 | 0.0217 | 5.94 |
| 12421.55 | 12420.55 | 42.543 | 0.4176 | 25.40 | 0.0438 | 13.11 |
| 12553.09 | 12552.08 | 42.770 | 0.3921 | 26.02 | 0.0446 | 12.44 |
| 12837.97 | 12836.97 | 43.255 | 0.7051 | 53.27 | 0.0904 | 22.92 |
| 13035.41 | 13034.40 | 43.589 | 0.2257 | 19.66 | 0.0331 | 7.46 |
| 13517.28 | 13516.27 | 44.393 | 1.7454 | 207.59 | 0.3436 | 60.20 |
| 13664.19 | 13663.19 | 44.635 | 1.0656 | 136.20 | 0.2239 | 37.24 |
| 13826.26 | 13825.25 | 44.901 | 0.9339 | 96.11 | 0.1572 | 33.11 |
| 14005.24 | 14004.23 | 45.193 | 4.3241 | 437.10 | 0.7106 | 155.80 |
| 14103.83 | 14102.82 | 45.353 | 2.4578 | 213.14 | 0.3450 | 89.36 |
| 14335.82 | 14334.81 | 45.727 | 8.7632 | 1030.75 | 1.6560 | 325.47 |
| 14534.46 | 14533.45 | 46.045 | 2.5813 | 335.53 | 0.5351 | 97.66 |
| 14717.09 | 14716.08 | 46.335 | 0.8605 | 197.18 | 0.3118 | 33.12 |
| 15187.24 | 15186.24 | 47.075 | 0.4437 | 75.60 | 0.1177 | 17.87 |
| 15657.41 | 15656.40 | 47.803 | 0.0897 | 8.45 | 0.0130 | 3.78 |
| 15820.39 | 15819.38 | 48.053 | 0.0865 | 9.75 | 0.0149 | 3.71 |
| 16443.65 | 16442.64 | 48.997 | 0.1190 | 11.73 | 0.0176 | 5.45 |
| 17066.08 | 17065.07 | 49.923 | 1.3076 | 165.52 | 0.2444 | 64.05 |
| 17175.08 | 17174.07 | 50.083 | 2.5670 | 301.87 | 0.4434 | 127.30 |
| 17296.48 | 17295.47 | 50.261 | 2.7701 | 417.80 | 0.6109 | 139.28 |
| 17482.10 | 17481.09 | 50.532 | 1.0341 | 142.54 | 0.2072 | 53.11 |
| 17766.54 | 17765.53 | 50.944 | 0.6228 | 131.11 | 0.1894 | 33.08 |
| 17945.02 | 17944.01 | 51.201 | 0.6698 | 282.23 | 0.4026 | 36.33 |
| 21092.56 | 21091.55 | 55.543 | 0.1325 | 101.64 | 0.1341 | 11.26 |
| 23718.05 | 23717.04 | 58.924 | 0.0883 | 65.37 | 0.0812 | 13.41 |
| 25789.62 | 25788.62 | 61.462 | 0.0509 | 34.02 | 0.0407 | 10.83 |
| 27804.46 | 27803.45 | 63.835 | 2.9497 | 1524.96 | 1.7606 | 669.03 |
| 28548.76 | 28547.75 | 64.689 | 0.8053 | 668.67 | 0.7571 | 187.12 |
| 31256.57 | 31255.56 | 67.709 | 0.0260 | 14.77 | 0.0161 | 6.61 |
| 32717.17 | 32716.17 | 69.284 | 0.0180 | 7.30 | 0.0078 | 4.81 |
| 34145.25 | 34144.24 | 70.791 | 0.1024 | 84.34 | 0.0879 | 28.83 |
| 34918.38 | 34917.37 | 71.593 | 0.0511 | 38.33 | 0.0394 | 14.78 |
| 37428.16 | 37427.16 | 74.139 | 0.0394 | 67.81 | 0.0677 | 12.55 |
| 39114.93 | 39113.92 | 75.802 | 0.0493 | 57.70 | 0.0560 | 16.80 |
| 41845.54 | 41844.54 | 78.421 | 0.1089 | 116.05 | 0.1097 | 40.17 |
| 42589.26 | 42588.26 | 79.120 | 0.0904 | 94.91 | 0.0883 | 33.69 |
| 44703.94 | 44702.93 | 81.073 | 0.0546 | 86.72 | 0.0788 | 20.98 |
| 50260.95 | 50259.94 | 85.996 | 0.0194 | 29.77 | 0.0255 | 8.06 |
| 55322.52 | 55321.51 | 90.250 | 0.1770 | 349.83 | 0.2859 | 79.52 |
| 65162.70 | 65161.69 | 97.996 | 0.0237 | 72.94 | 0.0551 | 11.64 |
| 69555.70 | 69554.69 | 101.264 | 0.0206 | 80.68 | 0.0584 | 10.46 |
| 82925.12 | 82924.12 | 110.623 | 0.0246 | 73.37 | 0.0490 | 13.93 |
| 89416.65 | 89415.64 | 114.894 | 0.0060 | 23.19 | 0.0148 | 3.43 |
| 97397.95 | 97396.94 | 119.939 | 0.0063 | 12.81 | 0.0079 | 3.57 |
| 110339.51 | 110338.50 | 127.698 | 0.0057 | 46.50 | 0.0263 | 3.26 |

Example 2

Incubation of Library with Unfractionated, Undiluted Human Pooled Plasma

To aid analysis of complex samples, this method is useful to decrease the concentration differential. Human plasma is one of the most complex and difficult to analyze materials: proteins are present in concentration range greater than $10^{10}$ (Anderson and Anderson); decreasing this range will aid in the analysis of trace proteins. Under the conditions of this method, incubation of plasma with the ligand library will increase the number of proteins that can be detected and subsequently analyzed as compared with analysis of the unprocessed starting material.

A. Sample Preparation

Frozen, pooled, human platelet-poor plasma (PPP) was thawed at 37° C. and filtered through 0.8 and 0.45 μm filters. Four replicates of approximately 1 ml of a library of hexamer peptide ligands on Toyopearl 650 M amino resin (65 μm average diameter, ~2×10⁶ beads/ml; Tosoh Biosciences, Montgomeryville, Pa.) with EACA-Ala spacer were each incubated with 9 ml of plasma for 1 hour at room temp, rotating. The resin was drained and washed with 1 ml citrate buffer (20 mM citrate, 140 mM NaCl, pH 7.0). This wash solution was retained, as well as samples of the loading plasma and initial flow through. Bead libraries were subsequently washed with 20 column volumes of citrate.

100 μl of resin from samples 2 and 4 were incubated with an equal volume (100 μl) of 2×LDS buffer+DTT (Invitrogen, Carlsbad, Calif.) for 10 minutes at 90° C. and centrifuged. The supernatant was collected and saved for analysis.

200 μl of resin from replicates 1-4 were incubated with 400 μl 6M GuHCl or 400 μl 6M urea for 1 hour in a batch format. The resin was allowed to drain and the flow through was collected for analysis. The GuHCl and urea concentrations in the eluates were reduced to 1M Urea on G-25 columns as follows: the G-25 columns were equilibrated twice with 200 μl 1M urea for 5 minutes, then centrifuged at 2000 rpm for 3 minutes. 20 μl of the urea and GuHCl samples were added to the tubes and centrifuged again under the same conditions. The flow through was collected.

B. LDS-PAGE Analysis

Figure 4:
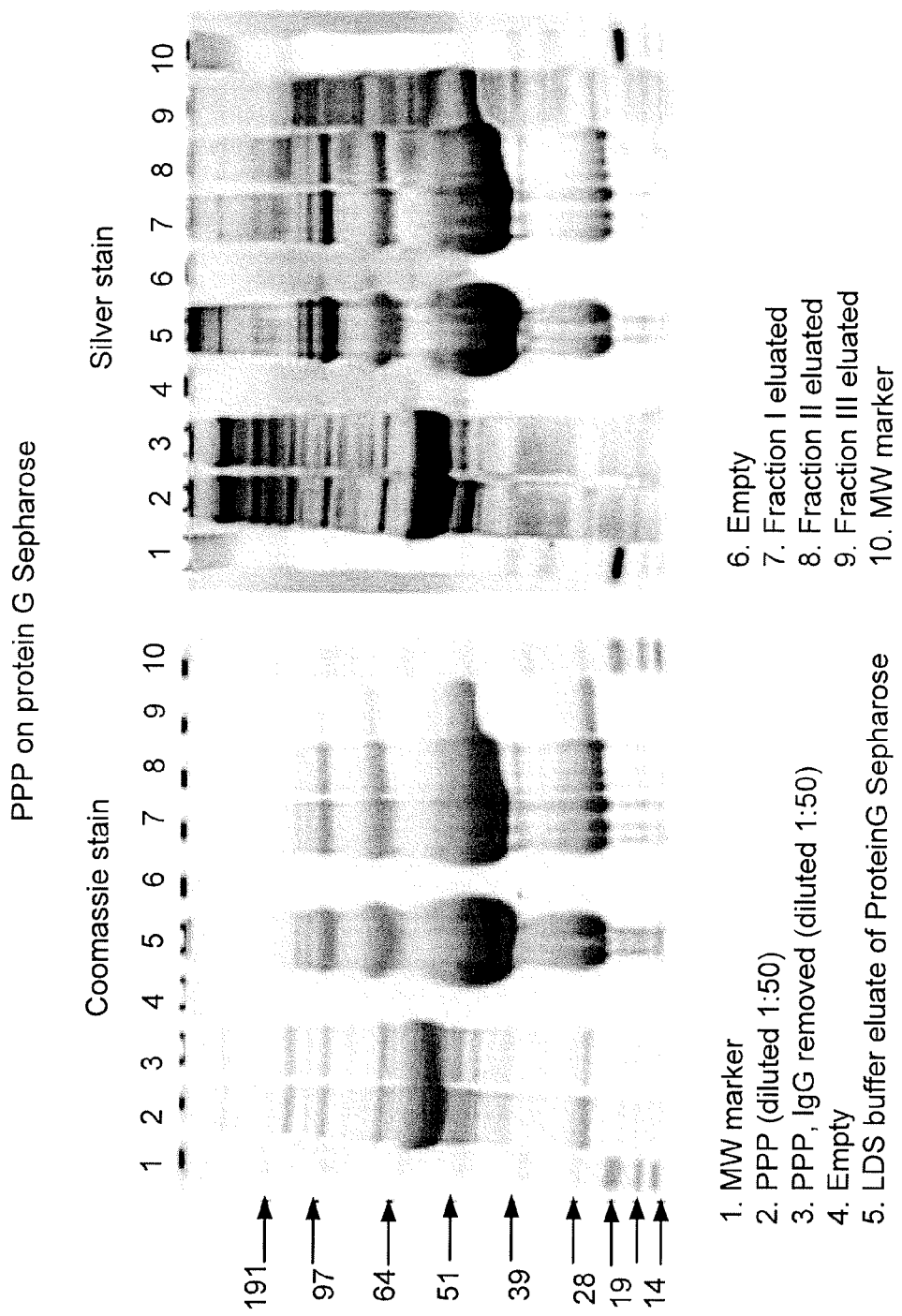
FIG. 4 is a PAGE analysis of Protein G column retentate. The panel on the left is stained with Coomassie Blue stain; the panel on the right is the same gel stained with Silver Quest.

Initial PPP, flow through and wash were diluted 1:25 with citrate buffer, then 1:2 with 2× sample buffer. 14 μl of the treated GuHCl and urea supernatants were heated in 5 μl 4×LDS buffer+2 μl DTT reducing agent for 10 minutes at 90° C. Two wells were loaded with approximately 10 μl of beads from samples 2 and 4.23 μl of each of the remaining samples were run on a 4-12% Bis-Tris gel (NuPage, Invitrogen) in MOPS buffer at 200 V. The gels were stained with Simply Blue (Invitrogen) according to the manufacturer's instructions. The results are shown in FIGS. 1 and 4.

Several bands that are not visible in the original plasma are present in the treated samples, while the very intense albumin band present in the original plasma (~64 kD) is substantially reduced. These results demonstrate that the method described does decrease the concentration range of proteins as detected by this method, thereby increasing the number of proteins that can be detected and analyzed compared with analysis of the starting material.

Example 3

Reduction of Concentration Variance After Removal of IgG

In many proteomic applications, one of the first steps of sample preparation is removal of albumin and IgGs, as these high abundance proteins mask the detection of lower abundance species. Removal of these proteins, however, also often removes trace species associated with them, and also involves loss of sample. It would be advantageous to have a method of sample preparation that does not require IgG depletion before analysis. This example demonstrates that removal of IgGs is not required to visualize protein species that are not detected in intact plasma. The pattern of proteins detected in LDS-PAGE is compared in plasma that has and has not been depleted of IgGs.

A. Sample Preparation

Frozen, pooled, human platelet-poor plasma (PPP) was thawed at 37° C. and filtered through 0.8 and 0.45 μm filters. IgG was removed from the plasma as follows: 5 ml Protein G Sepharose Fast-flow resin (Amersham, T&S) was packed in a Bio-Rad column, 10 ml of filtered PPP was added to the at a 10 cm/h flow rate (controlled by a peristaltic pump) and the flow through was collected.

Approximately 1 ml library of hexamer peptide ligands on Toyopearl 650 M amino resin (65 μm average diameter, ~2×10$^6$ beads/ml; Tosoh Biosciences, Montgomeryville, Pa.) with EACA-Ala spacer was incubated with 9 ml of flow through (above) for 1 hour/room temp/rotating. Clots that formed during incubation were removed by hand. The resin was drained and washed with 1 ml citrate buffer (20 mM citrate, 140 mM NaCl, pH 7.0), followed by 10 ml T-citrate (citrate buffer+0.05% Tween-20) and 10 ml citrate buffer. The flow through and first 1 ml of wash were collected for analysis. The resin was divided into 3 approximately equal, 200 μl aliquots.

One resin aliquot was heated with an equal volume (200 μl) 2×LDS buffer+DTT (Invitrogen, Carlsbad, Calif.) for 10 minutes at 90° C. and centrifuged. The supernatant was collected and saved for analysis. The remaining resin aliquots were incubated with 500 μl 6M GuHCl or 500 μl 6M urea for 1 hour in batch format. The resin was allowed to drain and the flow through was collected for analysis.

The GuHCl and urea concentrations in the eluates were reduced from 6M to 1M concentration and half the original volume (2× concentrated) by buffer exchange over G-25 columns.

B. LDS-PAGE Analysis

Figure 2:
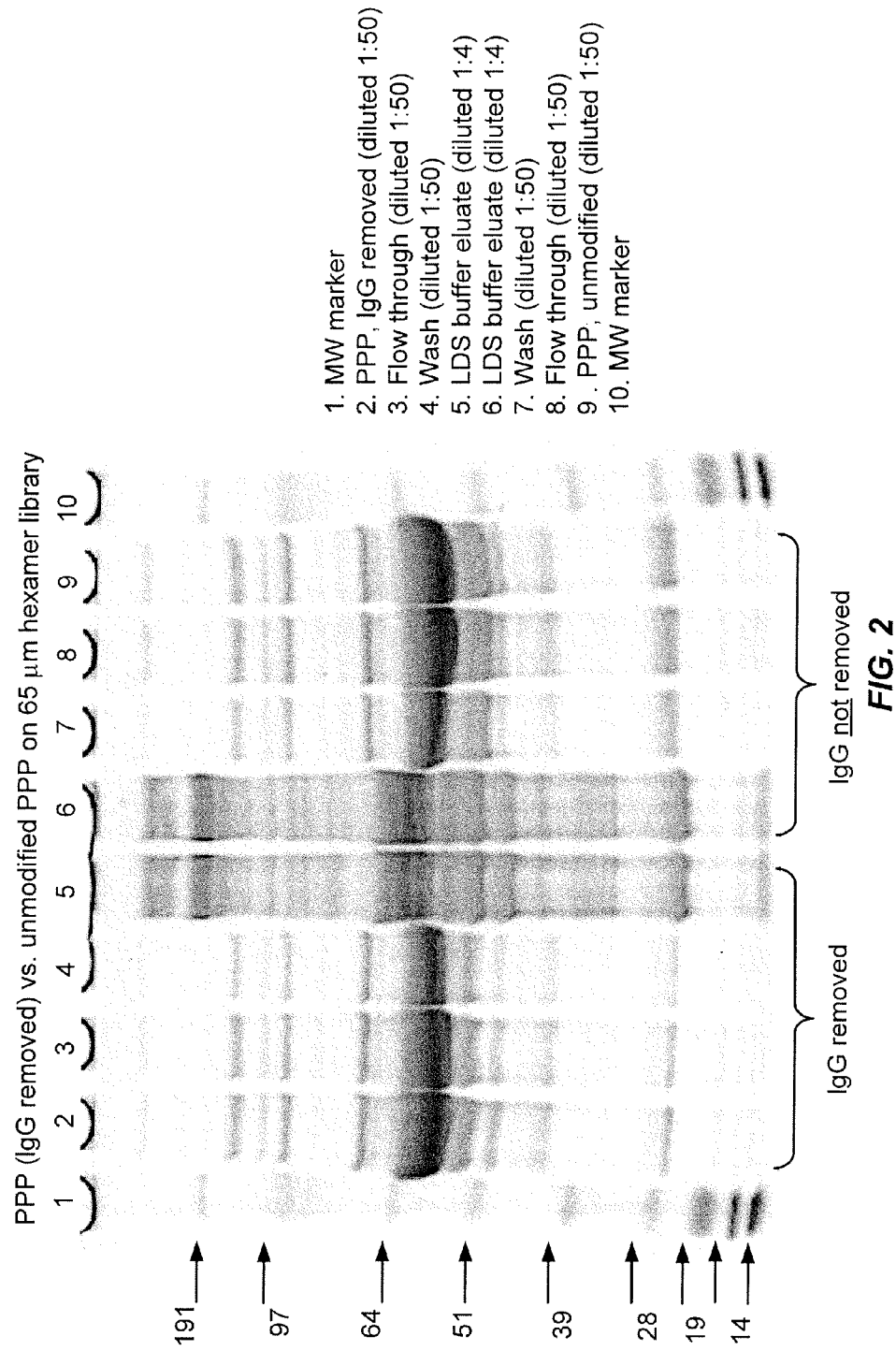
FIG. 2 is a comparison of plasma with and without removal of IgG prior to incubation with a library. The experiment was conducted as described in Example 3.

Initial PPP, IgG-depleted PPP, flow through and wash, as well as samples of GuHCl and urea supernatants were heated in LDS buffer+DTT reducing agent for 10 minutes at 90° C. The final dilutions of the LDS buffer, GuHCl, and Urea eluates were 0.25×, 1×, and 1×, respectively. The PPP, IgG-depleted plasma, flow through, and wash were diluted 50×. The Protein G LDS and Glycine eluates were incubated with 2×LDS buffer+DTT. 23 μl of each samples were run on a 4-12% Bis-Tris gel, in MOPS buffer, at 200 V. Samples of plasma prepared earlier according to the methods above from which the IgG was not removed were run as well. The gels were stained with Simply Blue followed by SilverQuest according to the manufacturer's instructions. The data is presented in FIG. 2.

Although in the starting, flow through and wash samples there is a clear decrease in proteins at MW 50 and 25 KDa (sizes of the reduced immunoglobulin heavy and light chains), there are no significant differences in the LDS-PAGE eluates from plasma both with and without IgG as visualized on the gels. The signals from the urea and GuHCl samples are indistinct due to sample handling issues. These data indicate that there is no obvious effect of removing IgGs. There may be other reasons that it is preferable to remove and retain the IgGs, perhaps for independent analysis; however, removal does not appear to be required to analyze trace proteins by this method.

Example 4

Reduction of Range of Concentrations of Proteins in Human Serum

Previous examples have demonstrated the usefulness of the described method with undiluted and unfractionated human plasma. In clinical diagnostics the starting sample frequently is serum, not plasma. The following example demonstrates the feasibility of using the described method to prepare serum for analysis.

A. Serum Preparation

Five 7 ml tubes of human blood were allowed to clot at 4° C. overnight. The clotted blood was centrifuged at 4,000 rpm for 5 minutes in a Sorvall centrifuge RT7, serum collected, and filtered through 0.8 and 0.45 μm filters.

B. Sample Preparation:

1. TentaGel-Based Library Incubation

250 μl of TentaGel library [TentaGel M NH$_2$ 10 μm (Rapp Polymer) library (Peptides International, Louisville, Ky.) with Gly spacer-10 μm average diameter, ~5.6×10$^8$ beads/ml] in a 15 ml conical tube was incubated with 2.25 ml (1:9 v/v) serum for 1 hour, at room temperature (RT). Resin was centrifuged at 4000 rpm for 2 minutes and the supernatant saved for analysis (FT Tenta). The beads were washed with 1.25 ml citrate buffer by shaking, then centrifuging at 4,000 rpm for 2 minutes in a 2 ml Eppendorf tube. Saved wash for analysis (W Tenta). The beads were washed with an additional 4×1.25 ml citrate buffer. The beads were divided into three approximately 75 μl aliquots.

One resin aliquot was incubated with 75 μl of 2×LDS/DTT, for 10 min, at 90° C. The beads were centrifuged and supernatant stored at −20° C. The others were incubated with 200 μl 6 M urea or 6 M GuHCl for 1.5 hr at RT. The initial and unbound serum fractions were diluted 1:25 with citrate, then 1:2 with 2×LDS/DTT. Samples were heated for 10 min at 90° C. and then frozen at −20° C.

2. Toyopearl-Based Library Incubation

Approximately 1 ml Toyopearl library (65 μm average diameter, ~2×106 beads/ml; Tosoh Biosciences, Montgomeryville, Pa.) was incubated with 9 ml serum for 1 hour/RT/rotating. 200 μl of resin were heated with 200 μl 2×(LDS buffer+DTT reducing agent) for 10 minutes at 90° C. The supernatant was collected and saved at −20C for analysis. 200 μl of resin were incubated with 400 μl (v/v) 6M urea for 1 hour in batch format. The flow through was collected for analysis and kept at room temperature. 200 μl of resin were incubated with 400 μl 6M GuHCl, for 1 hour in batch format. The flow through was collected for analysis and kept at room temperature. The initial and unbound serum fractions were diluted 1:25 with citrate, then 1:2 with 2×LDS/DTT. Samples were heated for 10 min at 90° C. and then frozen at −20° C. 200 μl serum and 200 μl of each unbound fraction were delivered to Analytical Chemistry for analysis.

C. LDS-PAGE Analysis

Figure 3:
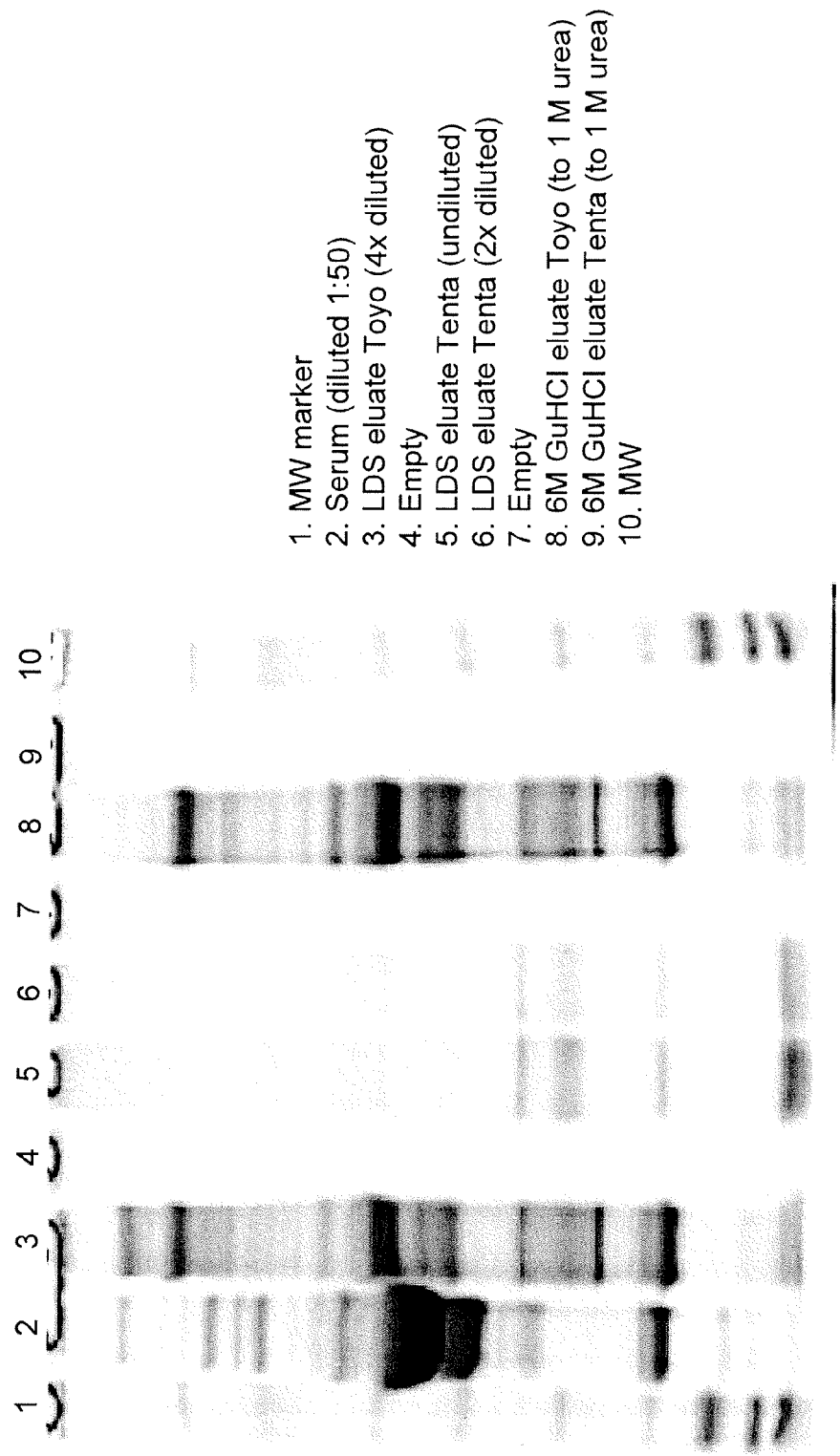
FIG. 3 depicts the result of an incubation of a combinatorial ligand library of the invention with serum. The experiment was conducted according to Example 4.

14 μl of 1 M urea and GuHCl samples were heated with 5 μl 4×LDS buffer and 2 μl 10×DTT for 10 min, at 90° C. The frozen LDS samples were re-heated for 10 min, at 90° C. 20 μl of each sample was loaded per well into two 4-12% Bis Tris gels. The gels were run with MOPS running buffer at 200 V until the dye front reached the bottom of gels. Gels were stained with Simply Blue protein stain according to the manufacturer's instructions and destained with H$_2$O. The gels are presented in FIG. 3.

There is a substantial increase in the number of bands visible in serum following incubation with library (compare lane 2 with lanes 3 and 8). The pattern of bands is very similar to the pattern obtained with incubation of library with plasma (compare lane 3, FIG. 3, with lane 7, FIG. 1). These results indicate that preparation of serum samples with the method of this invention increases the number of bands that can be analyzed by LDS-PAGE, and decreases the concentration of the mot abundant proteins in the eluates as compared with the starting serum.

Although the foregoing invention has been described in some detail by way of illustration and example for clarity and understanding, it will be readily apparent to one of ordinary skill in the art in light of the teachings of this invention that certain changes and modifications may be made thereto without departing from the spirit and scope of the appended claims.

All publications and patent applications cited in this specification are herein incorporated by reference as if each individual publication or patent application were specifically and individually indicated to be incorporated by reference.

What is claimed is:

1. A method for analyzing a biological extract containing a plurality of analyte species to detect said analyte species by a selected detection system, wherein said analyte species are present in said biological extract at concentrations encompassing such a wide range that analytes with concentrations at the upper end of said range, defined as high-abundance analyte species, interfere with the ability of said detection system to detect analyte species with concentrations at the lower end of said range, defined as low-abundance analyte species, said method comprising:
   (a) contacting a sample of said biological extract with a library of binding moieties, wherein said binding moieties are coupled to a solid support or supports, and said library of binding moieties having binding affinities sufficiently diverse to bind analyte species whose concentrations in said biological extract extend throughout said range, said sample and said library being at relative amounts such that said moieties that bind said high-abundance analyte species bind only a portion of said high-abundance analyte species, and by said binding produce a range of concentrations of bound analyte species that is sufficiently compressed relative to said range in said biological extract that interference by said high-abundance analyte species in said bound analyte species with the ability of said detection system to detect said low-abundance analyte species in said bound analyte species is substantially reduced and the number of analyte species detectable by said selected detection system is increased relative to the number of analytes species detectable by said selected detection system in said biological extract prior to contacting the sample of the biological extract with the library of binding moieties; and
   (b) isolating the analyte species that have bound to said binding moieties from components of said sample that did not so bind, and detecting by said selected detection system the analyte species that have so bound.

2. The method of claim 1 wherein said sample of said biological extract comprises at least 100, at least 1,000, at least 10,000, at least 1,000,000, or at least 10,000,000 analyte species.

3. The method of claim 1 wherein said library comprises at least 100, at least 1,000, at least 10,000, at least 1,000,000, or at least 10,000,000 binding moieties.

4. The method of claim 1 wherein said binding moieties are bio-organic polymers selected from peptides, oligonucleotides, and oligosaccharides.

5. The method of claim 1 wherein the library is a combinatorial library.

6. The method of claim 1 wherein the number of analyte species detectable by said selected detection system is increased by at least a factor of from two to four.

7. The method of claim 1 wherein said biological extract is selected from the group consisting of amniotic fluid, blood, cerebrospinal fluid, intraarticular fluid, intraocular fluid, lymphatic fluid, milk, perspiration plasma, saliva, semen, seminal plasma, serum, sputum, synovial fluid, tears, umbilical cord fluid, urine, biopsy homogenate, cell culture fluid, cell extracts, cell homogenate, conditioned media, fermentation broth, and tissue homogenate.

8. The method of claim 1 wherein said analyte species are selected from the group consisting of polypeptides, nucleic acids, complex carbohydrates, complex lipids, synthetic inorganic compounds, and synthetic organic compounds.

9. The method of claim 1, further comprising fractionating said analyte species so isolated.

10. The method of claim 1, further comprising contacting said isolated analyte species with a biospecific binding moiety and determining whether an analyte species is captured thereby.

11. The method of claim 1 wherein said binding moieties are selected from antibodies and aptamers.

12. The method of claim 1 wherein said solid support or supports is a collection of beads or particles.

13. The method of claim 1 wherein said solid support or supports is selected from fibers, monoliths, membranes, and plastic strips.

14. The method of claim 1 wherein said library is selected from a germline antibody library, a phage display library of recombinant binding proteins, a dye library, a non-combinatorial library in which the binding specificity of the members is not pre-selected, and a combinatorial library.

15. The method of claim 5 wherein the combinatorial library is a hexapeptide library.

16. The method of claim 1 wherein said selected detection system is selected from colorimetric, spectrophotometric, magnetic resonance, ellipsometric, mass spectroscopic, electrophoretic, chromatographic, enzymatic, and sequence analysis systems.

17. The method of claim 9 comprising fractionating said analytical molecules by a fractionation technique selected from chromatography, electrophoresis, filtration, and precipitation.

18. The method of claim 12 wherein each bead or particle has coupled thereto a binding moiety different from binding moieties coupled to all other beads or particles.

19. The method of claim 12 wherein a plurality of binding moieties having different binding affinities are coupled to a common bead or particle.

20. The method of claim 12 wherein each bead or particle has a diameter less than 1 μm.

21. The method of claim 12 wherein said beads or particles are coupled to a second solid support to form an array on said second solid support.

22. The method of claim 1 wherein said detection of step (b) is performed in a single analysis.

23. A method for identifying a diagnostic biomarker, the method comprising the steps of:
   (a) performing the method of claim 1 on a first set of biosamples from a first set of organisms having a first phenotype, and on second set of biosamples from a second set of organisms having a second phenotype;
   (b) identifying at least one analyte species whose concentration in the bound analyte species from said first set of biosamples differs from the concentration of said at least one analyte species in the bound analyte species from said second set of biosamples, and defining said at least one analyte species as said diagnostic biomarker distinguishing said first phenotype from said second phenotype.

24. The method of claim 23 wherein step (b) comprises identifying a biomarker profile that is distinguishable between said first phenotype from said second phenotype than any single biomarker.

25. The method of claim 1 wherein said biological extract is plasma.

26. The method of claim 1 wherein said biological extract is serum.

27. The method of claim 1 wherein said binding moieties are coupled to a solid packing material in a packed column.

28. The method of claim 27 wherein said packed column is a gravity column.

29. The method of claim 1 wherein said library is a combinatorial library produced by a split-and-pool process.

30. The method of claim 1 wherein step (b) is performed by eluting said analyte species so bound with an elution buffer.

31. The method of claim 1, further comprising identifying at least one of said analyte species so isolated by mass spectroscopy.

32. The method of claim 1, further comprising identifying at least one of said analyte species so isolated by a member selected from the group consisting of MALDI, MALDI-TOF, ESI, or SELDI.

33. The method of claim 1, further comprising identifying at least one of said analyte species so isolated by gel electrophoresis.

34. The method of claim 1, further comprising identifying at least one of said analyte species so isolated by two-dimensional gel electrophoresis.

35. The method of claim 1 wherein said range of analyte species concentrations in said in said biological extract spans at least four orders of magnitude.

36. The method of claim 1 wherein said analyte species that have bound to said binding moieties in step (a) have a range of analyte species concentrations that is decreased by at least a factor of two relative to said range of analyte species concentrations in said biological extract.

37. The method of claim 1 wherein said analyte species that have bound to said binding moieties in step (a) have a range of analyte species concentrations that is decreased by at least a factor of ten relative to said range of analyte species concentrations in said biological extract.

38. The method of claim 1 wherein said analyte species that have bound to said binding moieties in step (a) have a range of analyte species concentrations that is decreased by at least a factor of 100 relative to said range of analyte species concentrations in said biological extract.

39. The method of claim 1 wherein said analyte species are polypeptides.

40. The method of claim 39 wherein said library of binding moieties is a polypeptide library.

* * * * *